United States Patent
Keane et al.

(10) Patent No.: US 9,512,209 B2
(45) Date of Patent: *Dec. 6, 2016

(54) METHODS OF MODULATING INFLAMMASOME ACTIVITY TO TREAT INFLAMMATORY CONDITIONS

(71) Applicant: UNIVERSITY OF MIAMI, Miami, FL (US)

(72) Inventors: Robert W. Keane, Miami, FL (US); W. Dalton Dietrich, Miami, FL (US); Juan Pablo De Rivero Vaccari, Miami, FL (US); Helen M. Bramlett, Miami, FL (US)

(73) Assignee: University of Miami, Miami, FL (US)

( * ) Notice: Subject to any disclaimer, the term of this patent is extended or adjusted under 35 U.S.C. 154(b) by 37 days.

This patent is subject to a terminal disclaimer.

(21) Appl. No.: 14/219,857

(22) Filed: Mar. 19, 2014

(65) Prior Publication Data

US 2014/0286956 A1 Sep. 25, 2014

Related U.S. Application Data

(63) Continuation of application No. 12/182,886, filed on Jul. 30, 2008, now Pat. No. 8,685,400.

(60) Provisional application No. 60/952,757, filed on Jul. 30, 2007.

(51) Int. Cl.
*A61K 39/395* (2006.01)
*C07K 16/18* (2006.01)
*A61K 39/00* (2006.01)

(52) U.S. Cl.
CPC ............ *C07K 16/18* (2013.01); *A61K 39/395* (2013.01); *A61K 2039/505* (2013.01); *C07K 2317/76* (2013.01); *C07K 2317/77* (2013.01)

(58) Field of Classification Search
CPC .. C07K 16/18; C07K 16/244; C07K 16/245; C07K 2317/76; C07K 2317/77; C07K 2316/96; A61K 2039/505; A61K 39/395
See application file for complete search history.

(56) References Cited

U.S. PATENT DOCUMENTS

| | | | |
|---|---|---|---|
| 5,919,453 | A | 7/1999 | Benoit |
| 6,756,196 | B2 | 6/2004 | Bertin |
| 6,869,775 | B2 | 3/2005 | Bertin |
| 6,953,691 | B2 | 10/2005 | Reed |
| 8,685,400 | B2 | 4/2014 | Keane et al. |
| 2003/0077699 | A1 | 4/2003 | Reed |
| 2003/0224438 | A1 | 12/2003 | Bertin |
| 2003/0228570 | A1 | 12/2003 | Yat Wah Tom et al. |
| 2004/0053292 | A1 | 3/2004 | Tschopp et al. |
| 2004/0191247 | A1 | 9/2004 | Shohami |
| 2005/0202422 | A1 | 9/2005 | Tang et al. |
| 2005/0287570 | A1 | 12/2005 | Mounts |
| 2005/0287579 | A1 | 12/2005 | Wolfner et al. |
| 2006/0257952 | A1 | 11/2006 | Pestlin et al. |

FOREIGN PATENT DOCUMENTS

JP 2001-275681 10/2001
WO WO 2006/066917 6/2006

OTHER PUBLICATIONS

Davis BK et al. (2011) The inflammsome NLRs in immunity, inflammation, and associated diseases. Annu. Rev. Immunol. 29:707-735.*
Li X et al. Chronic behavioral testing after focal ischemia in the mouse: functional recovery and the effects of gender. Exp. Neurol. 2004, 187:94-104.*
Mariathasan, S. et al., Inflammasome adaptors and sensors: intracellular regulators of infection and inflammation, Nature Reviews/Immunology, 7(1):31-40 (Jan. 2007).
Petrilli, V, et al., The inflammasome, Curr. Biol., 15(15):R581 (Aug. 9, 2005).
Broadwell, R. D. et al., Serum proteins bypass the blood-brain fluid barriers for extrcellular entry to the central nervous system, Exp Neurol., 120:245-263 (1993).
de Rivero Vaccari, J. P. et al., A molecular platform in neurons regulates inflammation after spinal cord injury, The Journal of Neuroscience, 28(13):3404-3414 (Mar. 26, 2008).

(Continued)

*Primary Examiner* — Kimberly A. Ballard
(74) *Attorney, Agent, or Firm* — Cooley LLP

(57) ABSTRACT

Compositions and methods for reducing inflammation in the central nervous system (CNS) of a mammal that has been subjected to a stroke, traumatic injury to the CNS such as traumatic brain injury (TBI), spinal cord injury (SCI), or having an autoimmune or CNS disease have been developed. The compositions and methods described herein include antibodies that specifically bind to at least one component (e.g., ASC, NALP1) in a mammalian inflammasome (e.g., the NALP1 inflammasome) and have use as treatments for SCI, TBI, stroke, and autoimmune and CNS diseases in a mammal. In a rodent model of SCI, therapeutic neutralization of ASC using a polyclonal antibody that specifically binds to ASC inhibited the inflammasome, reduced caspase-1 activation, XIAP cleavage, and interleukin processing, resulting in significant tissue sparing and functional improvement. Additionally, in a rodent model of TBI, neutralization of ASC after TBI reduced caspase-1 activation and XIAP cleavage. Further, in a rodent thromboembolic stroke model, neutralization of NLRP1 resulted in reduced histopathological damage in mice and reduced cytokine activation, suggesting that the inflammasome complex forms in the brain after stroke and is a therapeutic target for reducing the detrimental consequences of post-stroke inflammation.

19 Claims, 10 Drawing Sheets

(56) References Cited

OTHER PUBLICATIONS

Hauff, K. et al., Peptide-based approaches to treat asthma, arthritis, other autoimmune diseases and pathologies of the central nervous system, Arch Immunol Ther Exp., 53:308-320 (2005).

Agostini et al., NALP3 forms an IL-1B-processing inflammasome with increased activity in muckle-wells autoinflammatory disorder, Immunity, 20:319-325 (Mar. 2004).

Allan et al., Interleukin-1 and neuronal injury, Nature Reviews/Immunology, 5:629-640 (Aug. 2005).

Cimaz et al., IL1 and TNF gene polymorphisms in patients with juvenile idiopathic arthritis treated with TNF inhibitors, Ann Rheum Dis, 66:900-904 (2007).

Dinarello et al., Unraveling the NALP-3/IL-1B inflammasome: a big lesson from a small mutation, Immunity, 20:243-246 (Mar. 2004).

Dinarello et al., Therapeutic strategies to reduce IL-1 activity in treating local and systemic inflammation, Current Opinion in Pharmacology, 4:378-385 (2004).

Duncan et al., Cryopyrin/NALP3 binds ATP/dATP, is an ATPase, and requires ATP binding to mediate inflammatory singaling, PNAS, 104(19): 8041-8046 (May 8, 2007).

Huang et al., Increased expression of caspase-1 and interleukin-18 in peripheral blood mononuclear cells in patients with multiple sclerosis, Multiple Sclerosis, 10:482-487 (2004).

Kamm et al., The effect of traumatic brain injury upon the concentration and expression of interleukin-1B and interleukin-10 in the rat, J. Trauma, 60:152-157 (2006).

Keane et al., Apoptotic and anti-apoptotic mechanisms following spinal cord injury, Journal of Neuropathology & Experimental Neurology, 60(5),422-429 (May 2001).

Keane et al., Apoptotic and anti-apoptotic mechanisms after traumatic brain injury, Journal of Cerebral Blood Flow & Metabolism, 21:1189-1198 (2001).

Lai et al., Association of interleukin-1 gene cluster polymorphisms with ischemic stroke in a Chinese population, Neurol India, 54:366-369 (2006).

Lotocki et al., Inhibitors of apoptosis proteins in injury and disease, Life, 54:231-240 (2002).

Lotocki et al., Monoubiquitination and cellular distribution of XIAP in neurons after traumatic brain injury, Journal of Cerebral Blood Flow & Metabolism, 23:1129-1136 (2003).

Mariathasan et al., Cryopyrin activates the inflammasome in response to toxins and ATP, Nature, 440:228-232 (Mar. 9, 2006).

Martinon et al., The inflammasome: a molecular platform triggering activation of inflammatory caspases and processing of proIL-B, Molecular Cell, 10:417-426 (Aug. 2002).

Martinon et al., Inflammatory caspases and inflammasornes: master switches of inflammation, Cell Death & Differentiation, 14:10-22 (2007) (published on-line Sep. 15, 2006).

Martinon et al., Inflammatory caspases: linking an intracellular innate immune system to autoinflammatory diseases, Cell, 117:561-574 (May 28, 2004).

Martinon et al., Indentification of bacterial muramyl dipeptide as activator of the NALP3/cryopyrin inflammasome, Current Biology, 14:1929-1934 (Nov. 9, 2004).

Masumoto et al., ASC, a novel 22-kDa protein, aggregates during apoptosis of human promyelocytic leukemia HL-60 cells, J. of Biol. Chem., 274(48):33835-33838 (Nov. 26, 1999).

Masumoto et al., Expression of apoptosis-associated speck-like protein containing a caspase recruitment domain, a pyrin N-terminal homology domain-containing protein, in normal human tissues, Journal of Histochemistry & Cytochemistry, 49(10):1269-1275 (2001).

Masumoto et al., Caspy, a zebrafish caspase, activated by ASC oligomerization is required for pharyngeal arch development, J. of Biol. Chem., 278(6),4268-4276 (Feb. 7, 2003).

Nagatsu et al., Changes in cytokines and neurotrophins in Parkinson's Disease, J. Neural Transm Suppl., 60:277-290 (2000).

Ogura et al., The inflammasome: first line of the immune response to cell stress, Cell, 126:659-662, (Aug. 25, 2006).

Ooi et al., Cytokines and chemokines in uveitis-is there a correlation with clinical phenotype?, Clinical Medicine & Research, 4(4): 294-309 (2006).

Papin et al., The SPRY domain of Pyrin, mutated in familial Mediterranean fever patients, interacts with inflammasome components and inhibits proIL-1B processing, Cell Dealth & Differentiation, 14:1457-1466 (2007).

Rast et al., Genomic insights into the immune system of the sea urchin, Science, 314: 952-956 (2006).

Ravizza et al,, Inactivation of caspase-1 in rodent brain: a novael anticonvulsive strategy, Epilepsia, 47:1160-1168 (2006).

Shiohara et al., ASC, which is copmosed of a PYD and a CARD, is up-regulated by inflammation and apoptosis in human neutrophils, Biochemical & Biophysical Research Communications, 293:1314-1318 (2002).

Siegmund et al., IL-1B-converting enzyme (caspase-1) in intestinal inflammation, PNAS, 98(23)13249-13254 (Nov. 6, 2001).

Ting, J. P.-Y. et al., Caterpillers, pyrin and hereditary immunological disorders, Nature Reviews/Immunology, 6:183-195 (Mar. 2006).

Ting, J. P.-Y. et al., The NLR gene family: an official nomenclature, Immunity, 28(3):285-287 (Mar. 2008).

Tran, M. D. et al., Expression of P2 purinergic receptors in rat cortex after moderate traumatic brain injury, Neuroscience Program, The Miami Project to Cure Paralysis, Dept. of Neurological Surgery and Research Service, Virginia Medical Center and University of Miami School of Medicine, Miami, FL (2002).

Tschopp et al., NALPS: a novel protein family involved in inflammation, Nature Reviews/Molecular Cell Biology, 4:95-104 (Feb. 2003).

Wang, X. J. et al., Interleukin-1 beta induction of neuron apoptosis depends on p38 mitogen-activated protein kinase activity after spinal cord injury, Acta Pharmacologica Sinica, 26(8):934-942 (Aug. 2005).

Abcam PLC, Alternative names for TMS1 antibody (ab19219), [online] www.abcam.com/assets/popups/popup_alt_names.htm?intAbID=19219 ( printed Mar. 1, 2010).

AnaSpec, Inc., Anti-ASC (Apoptosis-associated speck-like protein containing a CARD, CARD5, TMS1), [online] Catalog No. 54065, www.anaspec.com/products/product.asp?id=36636, product information sheet.

Axxora Platform [online], www.axxora.com/inflammasome-ALX-210-905/opfa.1.1.ALX-210-905.1414.4.1.html, Anti-ASC Antibody (printed Mar. 8, 2010).

Chemicon [online], www.chemiconcustom.com/browse/productdetail.asp?ProductID=AB3607, Anti-ASC Antibody data sheet (printed Mar. 8, 2010).

Everest Biotech [online], www.everestbiotech.com/acatalog/EB05291.html, Abstract: EB05291 Goat Anti-ASC/TMS1 Antibody data sheet (printed Mar. 8, 2010).

Novus Biologicals [online], www.novusbio.com/data_sheet/print_data_sheet/12015, Anti-ASC Antibody data sheet (2009).

Xiang, Y. et al., IL-18 binding and inhibition of interferon γ induction by human poxvirus-encoded proteins, Proc. Natl. Acad. Sci. USA, 96:11537-11542 (Sep. 1999).

Tsutsui, H. et al., Caspace-1-independent, Fas/Fas ligand-mediated IL-18 secretion from macrophages causes acute liver injury in mice, Immunity, 11(3):359-367 (Sep. 1999) Abstract.

Yoshimoto, T. et al., LPS-stimulated SJL macrophages produce Il-12 and IL-18 that inhibit IgE production in vitro by induction of IFN-γ production from CD3intIL-2RB+ T cells, The Journal of Immunology, 161:1483-1492 (1998).

Hill, K. E. et al., Cerebellar purkinje cells incorporate immunoglobulins and immunotoxins in vitro: implications for human neurological disease and immunotherapeutics, Journal of Neuroinflammation, 6:31 (Oct. 29, 2009).

Karpiak, S. E. at al., Selective uptake by purkinje neurons of antibodies to S-100 protein, Experimental Neurology, 98:453-457 (1987).

(56) References Cited

OTHER PUBLICATIONS

Mikloska, Z. et al., Neutralizing antibodies inhibit axonal spread of herpes simplex virus type 1 to epidermal cells in iitro, Journal of Virology, p. 5934-5944 (Jul. 1999).

Dong, M. et al., Synaptotagmins I and II mediate entry of botulinum neurotoxin B into cells, The Journal of Cell Biology, 162(7):1293-1303 (Sep. 29, 2003).

* cited by examiner

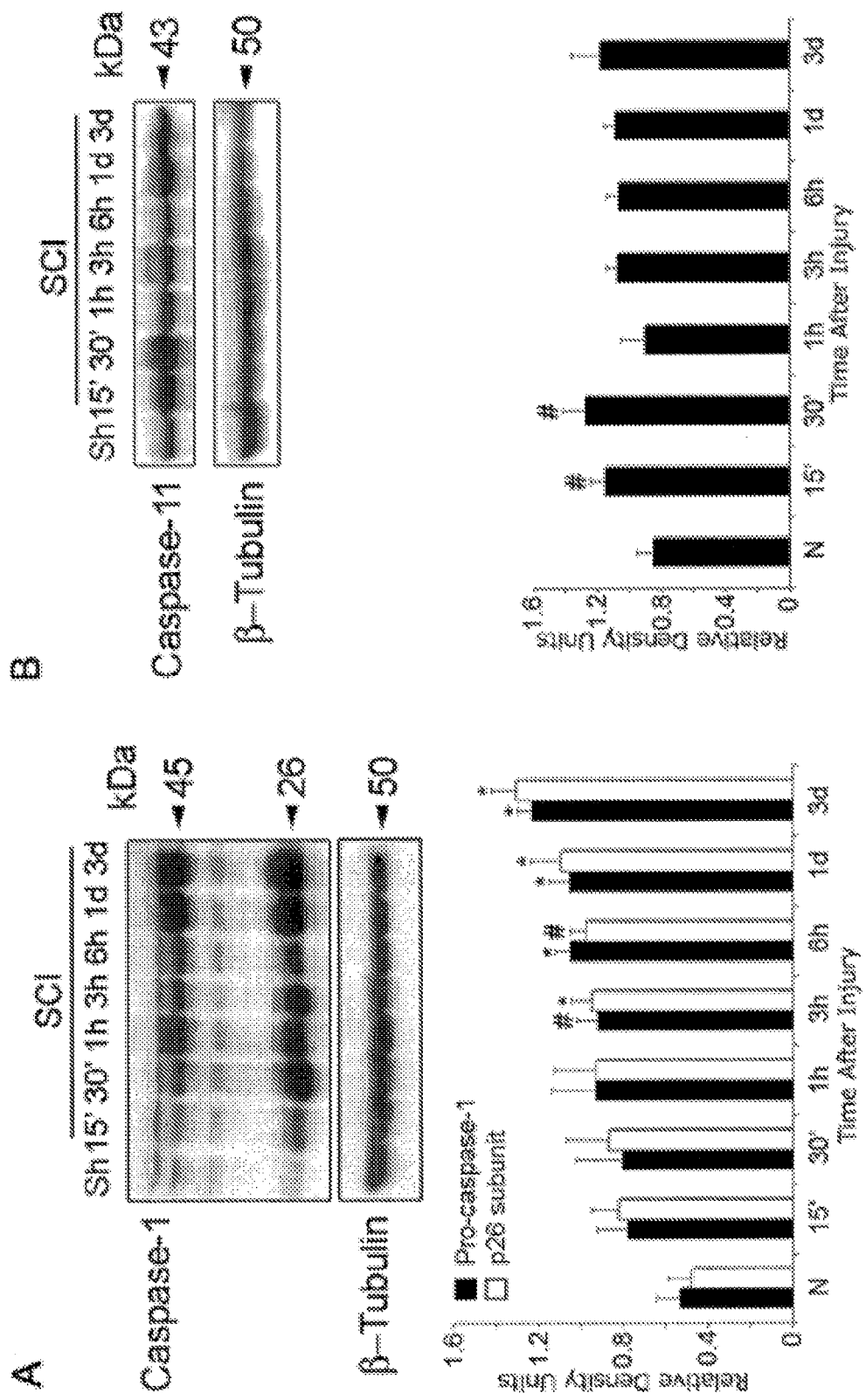
FIGURE 1A-B

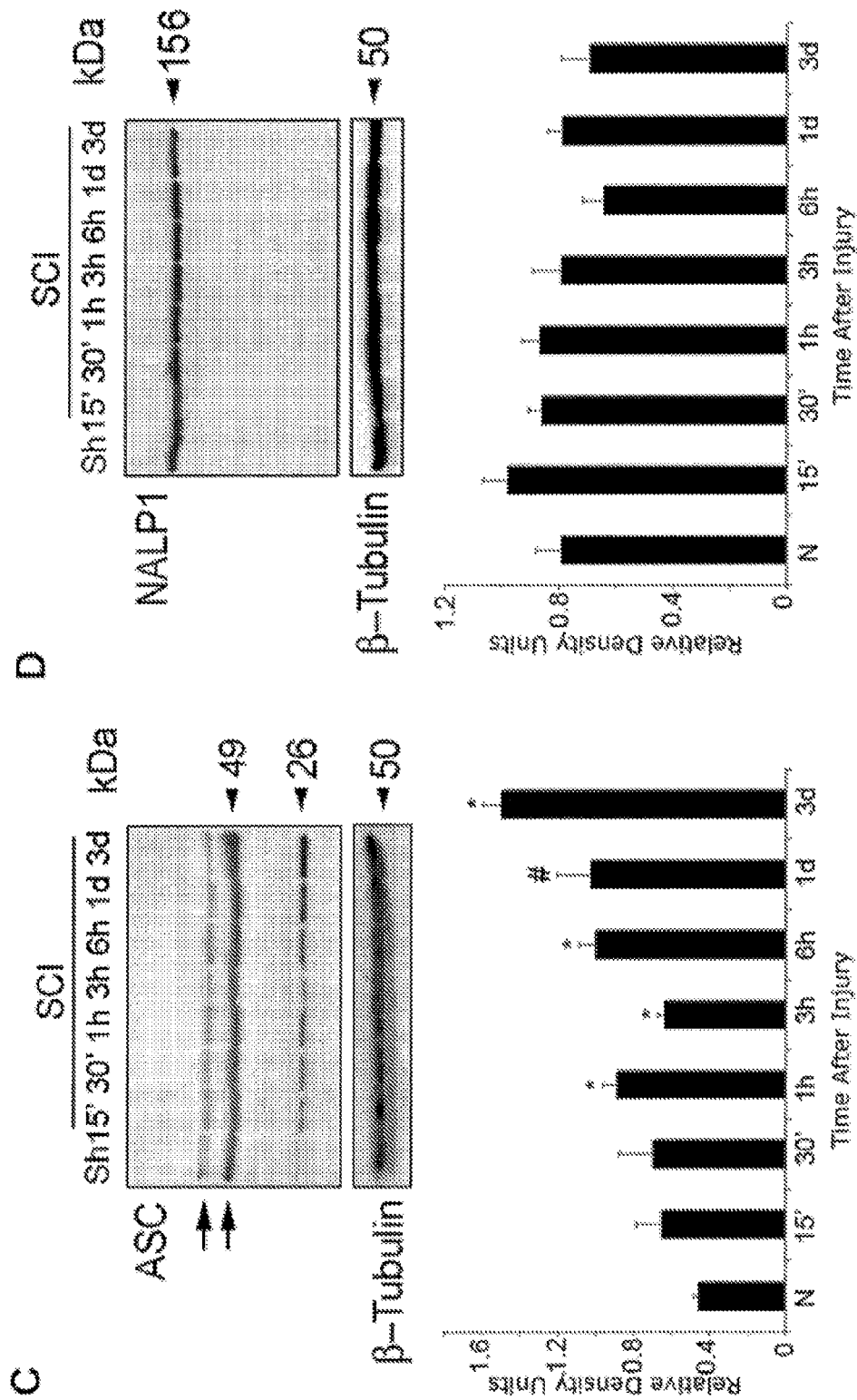
FIGURE 1C-D

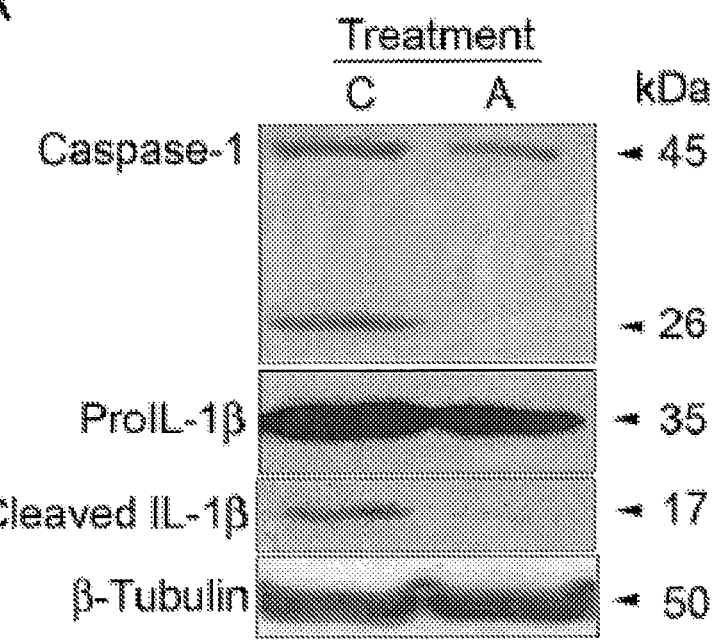
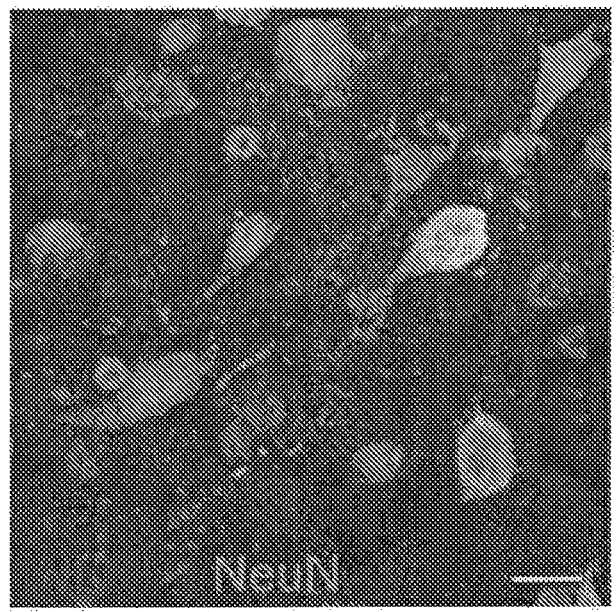
FIGURE 3A-B

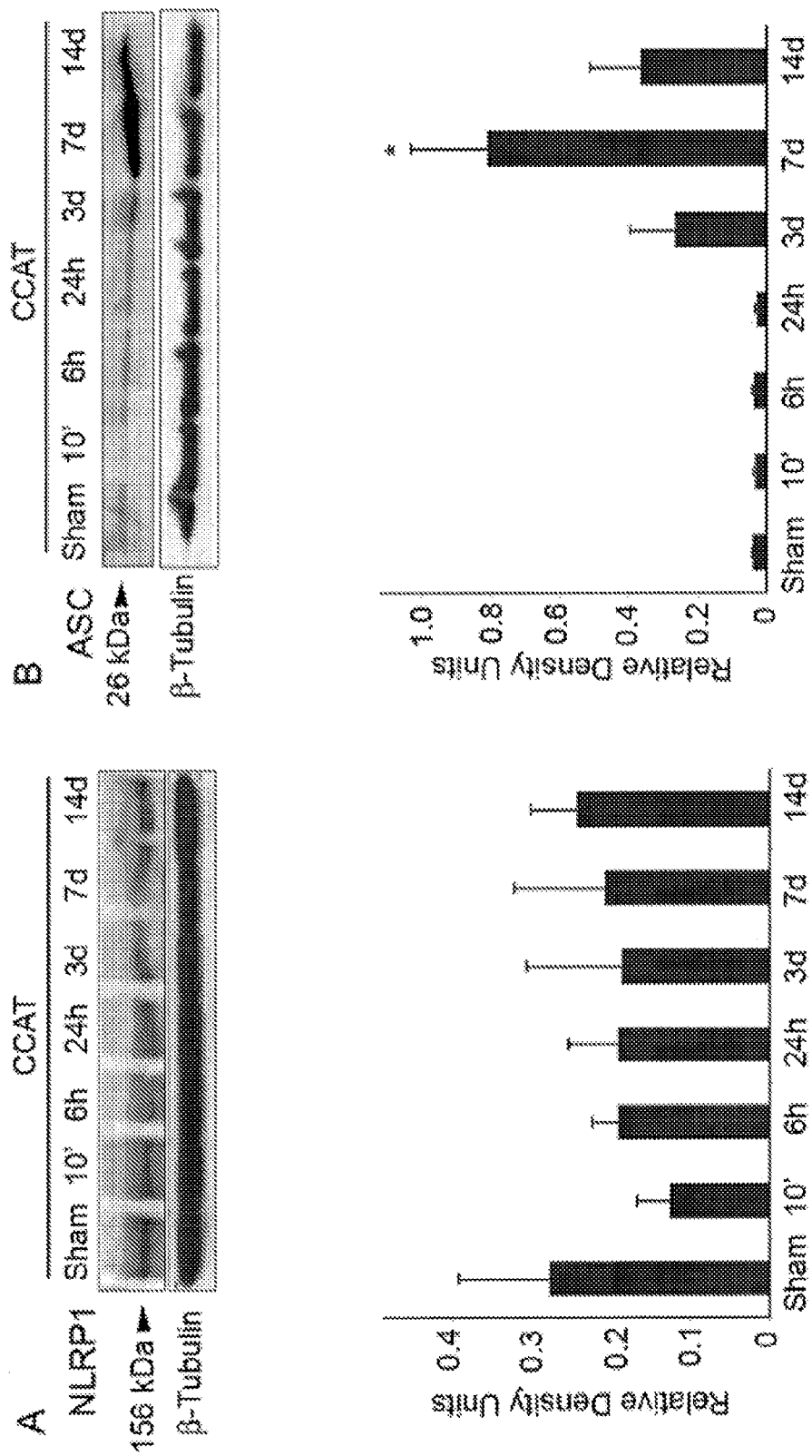
FIGURE 4A-B

SEQUENCE LISTING

<160> NUMBER OF SEQ ID NOS: 4

<210> SEQ ID NO 1
<211> LENGTH: 16
<212> TYPE: PRT
<213> ORGANISM: Rattus norvegicus

<400> SEQUENCE: 1

Ala Leu Arg Gln Thr Gln Pro Tyr Leu Val Thr Asp Leu Glu Gln Ser

```
<210> SEQ ID NO 2
<211> LENGTH: 14
<212> TYPE: PRT
<213> ORGANISM: Homo sapiens

<400> SEQUENCE: 2

Arg Glu Ser Gln Ser Tyr Leu Val Glu Asp Leu Glu Arg Ser
1               5                   10

<210> SEQ ID NO 3
<211> LENGTH: 19
<212> TYPE: PRT
<213> ORGANISM: Homo sapiens

<400> SEQUENCE: 3

Cys Glu Tyr Tyr Thr Glu Ile Arg Glu Arg Glu Arg Glu Lys Ser Glu
1               5                   10                  15

Lys Gly Arg

<210> SEQ ID NO 4
<211> LENGTH: 15
<212> TYPE: PRT
<213> ORGANISM: Rattus norvegicus

<400> SEQUENCE: 4

Met Glu Glu Ser Gln Ser Lys Glu Glu Ser Asn Thr Glu Gly Cys
1               5                   10                  15
```

METHODS OF MODULATING INFLAMMASOME ACTIVITY TO TREAT INFLAMMATORY CONDITIONS

CROSS-REFERENCE TO RELATED APPLICATIONS

The present application is a continuation of U.S. application Ser. No. 12/182,886, filed Jul. 30, 2008, now U.S. Pat. No. 8,685,400, which claims the priority of U.S. provisional application No. 60/952,757 filed on Jul. 30, 2007, both of which are hereby incorporated by reference in their entireties.

STATEMENT AS TO FEDERALLY SPONSORED RESEARCH

This invention was made with U.S. government support under grant number NS30291 awarded by the National Institutes of Health, grant number NS38865 awarded by the National Institute of Neurological Disorders and Stroke, and grant number W81XWH-05-1-6, awarded by the Department of Defense. The U.S. government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: UNMI_003_02US_SeqList_ST25.txt, date recorded: Mar. 19, 2014, file size 2 kilobytes).

FIELD OF THE INVENTION

The invention relates generally to the fields of immunology and medicine. More particularly, the invention relates to compositions and methods for modulating ASC (Apoptosis-associated Speck-like protein containing a Caspase Activating Recruitment Domain (CARD)) activity and NAcht Leucine-Rich-Repeat Protein 1 (NALP1) inflammasome activity in the central nervous system (CNS) of a mammal as treatments for reducing inflammation in response to injury to the CNS, including spinal cord injury (SCI), and traumatic brain injury (TBI), and for the treatment of stroke as well as autoimmune diseases and/or CNS diseases including amyotropic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD).

BACKGROUND

The CNS represents the largest part of the nervous system, including the brain and the spinal cord. Traumatic injury to the brain and spinal cord affect 1.4 million and between 10-12 thousand people, respectively, every year in the United States (U.S.). Direct medical costs and indirect costs such as loss of productivity associated with these injuries to the CNS costs billions of dollars annually in the U.S.

A TBI is defined as a blow or jolt to the head or a penetrating head injury that disrupts the function of the brain. The severity of such an injury may range from a brief change in mental status or consciousness to an extended period of unconsciousness or amnesia after the injury. TBI triggers a complex sequence of inflammatory responses that contribute to secondary injury, and has been defined as a predominantly immunological and inflammatory disorder. The endogenous neuroinflammatory response in the injured brain contributes to the breakdown of the blood-brain barrier, and to the development of posttraumatic cerebral edema, neuronal cell death, and to neuropathological sequalae which are, in large part, responsible for the adverse outcome.

Currently, no proven neuroprotective treatments for TBI exist. Although steroids, barbiturates and mild hypothermia have been reported to benefit some TBI patients, these treatments have failed in multi-center trials.

SCI is associated with physical and psychological disorder that causes disability and requires intensive treatment. In SCI, the initial physical trauma to the spinal cord sets off a cascade of biochemical and cellular events that kills neurons, strips axons of their myelin insulation, and triggers an inflammatory immune system response. Neurons continue to die for hours after SCI, and this secondary cell death is mediated by an immune response that activates and processes proinflammatory cytokines Interleukin-10 (IL-1β) and Interleukin-18 (IL-18). Another consequence of the immune system's entry into the CNS is that inflammation accelerates the production of highly reactive forms of oxygen molecules called free radicals. Free radicals are produced as a by-product of normal cell metabolism. In the healthy spinal cord their numbers are small enough that they cause no harm. But injury to the spinal cord, and the subsequent wave of inflammation that sweeps through spinal cord tissue, signals particular cells to overproduce free radicals. Free radicals then attack and disable molecules that are crucial for cell function (e.g., those found in cell membranes) by modifying their chemical structure. Free radicals can also change how cells respond to natural growth and survival factors, and turn these protective factors into agents of destruction.

Methylprednisolone, a steroid drug, is the standard treatment for acute SCI. Methylprednisolone appears to reduce the damage to nerve cells and decreases inflammation near the injury site by suppressing activities of immune cells. Methylprednisolone is effective only if used in high doses within eight hours of acute injury, however, high doses of methylprednisolone can lead to side effects, such as infections, and adverse effects on tissue recovery. Indeed, many clinicians feel that the adverse effects of methylprednisolone treatment outweigh the benefits. Thus, methylprednisolone is not routinely given to SCI patients in most large centers.

In traumatic injuries to the CNS, studies suggest that modulation of post-traumatic inflammation may provide the best opportunity to arrest the secondary injury cascade. At present, there are no pharmacologic strategies of proven benefit. Most of the neuroprotective agents are free radical scavengers and many inhibit only one or two aspects of inflammation. Few drugs are found to be effective at modulating inflammation in the CNS after traumatic injury, and their therapeutic benefit is hampered by side effects. Although steroids, for example, continue to be given to patients with SCI in many institutions, evidence of deleterious effects continues to accumulate.

In addition to TBI and SCI, ischemic stroke is an event in which inflammation plays a significant role in the pathology of the disease. More than 750,000 Americans have a stroke each year, making stroke the third leading cause of death in the U.S. Ischemic events initiated by thromboembolic processes such as stroke activate complex pathophysiological mechanisms that result in neurological deficits and neuronal cell death. The initial vascular responses to embolic events also lead to secondary injury mechanisms including inflammation that contributes to the damaging cellular and molecular responses of ischemic injury, e.g., the death of nerve cells. Currently, there are no neuroprotective drugs that have been approved for use in ischemic stroke patients.

The failure of currently available anti-inflammatory agents in offering significant neuroprotection in large epidemiologic clinical trials of CNS disorders suggests an urgent need for the development of new neuroprotective agents.

SUMMARY

The invention relates to the development of compositions and methods for reducing inflammation in the CNS of a mammal that has been subjected to a traumatic injury to the CNS such as TBI or SCI, or is suffering from a stroke, a neurodegenerative disease, or an autoimmune disease with an inflammatory component. The compositions and methods described herein include antibodies that specifically bind to at least one component (e.g., ASC, NLRP1) of a mammalian inflammasome (e.g., the NALP1 inflammasome) and have use as treatments for SCI, TBI stroke, autoimmune diseases, and neurodegenerative diseases in a mammal.

The inflammatory response initiated by SCI, TBI, and stroke involves activation of IL-1β that contributes to secondary cell death. In the peripheral immune response, the inflammasome activates caspase-1 to process proinflammatory cytokines The results of the experiments described herein show that components of the NALP1 inflammasome (also referred to as the "NLRP1 inflammasome", see Ting et al. Immunity 28:285-287, 2008 for nomenclature pertaining to this inflammasome and related proteins and protein complexes), including caspase-1, -11, ASC and NALP1 (also referred to as "NLRP1") are expressed in neurons of the normal rat spinal cord, and form a protein assembly with the X-linked inhibitor of apoptosis family member, XIAP. In a rodent model, moderate cervical contusive SCI induced processing of IL-1β, IL-18 and IL-33, activation of caspase-1, cleavage of XIAP, and promoted assembly of the NALP1 inflammasome. Therapeutic neutralization of ASC using a polyclonal antibody that specifically binds to ASC inhibited the inflammasome, reduced caspase-1 activation, XIAP cleavage, and interleukin processing, resulting in significant tissue sparing and functional improvement. Additionally, in a rodent model of TBI, neutralization of ASC after TBI reduced caspase-1 activation and XIAP cleavage. Further, in a rodent thromboembolic stroke model, neutralization of NLRP1 resulted in reduced histopathological damage in mice and reduced cytokine activation. These results show that the inflammasome complex forms in the brain after stroke and may be a therapeutic target for reducing the detrimental consequences of post-stroke inflammation. Thus, the NALP1 inflammasome constitutes an important arm of the innate CNS inflammatory response following SCI, TBI, and stroke.

Accordingly, described herein is a method of reducing inflammation in the CNS of a mammal having a CNS injury or disease (e.g., TBI, traumatic SCI, ischemic stroke, neurodegenerative disease, and autoimmune disease). The method includes the steps of: providing a therapeutically effective amount of a composition including an antibody that specifically binds to at least one component of a mammalian inflammasome (e.g., NALP1 inflammasome); and administering the composition to the mammal, wherein administering the composition to the mammal results in a reduction of caspase-1 activation in the CNS of the mammal. The composition can be administered, for example, intravenously, intraperitoneally, or intracerebroventicularly, and can further include at least one pharmaceutically acceptable carrier or diluent. The CNS injury or disease can be ALS, MS, immune dysfunction muscular central nervous system breakdown, MD, AD, and PD. In one embodiment of the method, the CNS injury or disease is SCI and the at least one component of the NALP1 inflammasome is Apoptosis-associated Speck-like protein containing a Caspase Activating Recruitment Domain protein (ASC) or NAcht Leucine-Rich-Repeat Protein 1 (NALP1). Administering the composition to the mammal can result in an improvement in motor skills and locomotor function in the mammal, as well as a decreased spinal cord lesion volume in the mammal.

In a typical method, the antibody binds to an amino acid sequence having at least 85% sequence identity with an amino acid of: SEQ ID NO:1, SEQ ID NO:2, SEQ ID NO:3 and SEQ ID NO: 4, and inhibits ASC or NALP1 activity in cells of the CNS in the mammal.

The CNS injury or disease can be ischemic stroke and the at least one component of the NALP1 inflammasome can be ASC or NLRP1. In this method, the composition is administered intracerebroventricularly, intraperitoneally or intravenously. Administration of the composition can result in a reduced infarct size in the mammal.

The CNS injury or disease can be a traumatic brain injury and the at least one component of the NALP1 inflammasome can be ASC or NALP1.

Also described herein is a method of reducing inflammation in the brain of a mammal that has been subjected to a TBI. The method includes the steps of: providing a therapeutically effective amount of a composition including an antibody that specifically binds to ASC or NALP1; and administering the composition to the mammal such that the antibody is taken up by cells in the brain, wherein administering the composition to the mammal results in a reduction of caspase-1 activation and XIAP cleavage in the brain of the mammal. In the method, the composition can include at least one pharmaceutically acceptable carrier or diluent and can be administered intracerebroventricularly, intravenously or intraperitoneally.

Further described herein is a method of treating a SCI in a mammal. The method includes the steps of: providing a therapeutically effective amount of a composition including an antibody that specifically binds to ASC or NALP1; and administering the composition to the mammal such that the antibody is taken up by neurons in the CNS, wherein administering the composition to the mammal results in an improvement in motor skills and locomotor function or cognition in the mammal. Administering the composition to the mammal results in a decreased spinal cord lesion volume in the mammal. The composition can include at least one pharmaceutically acceptable carrier or diluent and can be administered intravenously.

Unless otherwise defined, all technical terms used herein have the same meaning as commonly understood by one of ordinary skill in the art to which this invention belongs.

As used herein, "protein" and "polypeptide" are used synonymously to mean any peptide-linked chain of amino acids, regardless of length or post-translational modification, e.g., glycosylation or phosphorylation.

By the terms "Apoptosis-associated Speck-like protein containing a Caspase Activating Recruitment Domain (CARD)" and "ASC" is meant an expression product of an ASC gene or isoforms thereof, or a protein that shares at least 65% (but preferably 75, 80, 85, 90, 95, 96, 97, 98, or 99%) amino acid sequence identity with ASC (e.g., accession number BAC43754 in rat, accession number Q9ULZ3 in human) and displays a functional activity of ASC. A "functional activity" of a protein is any activity associated with the physiological function of the protein. Functional activities of ASC include, for example, recruitment of proteins for activation of caspase-1 and initiation of cell death.

By the term "ASC gene," or "ASC nucleic acid" is meant a native ASC-encoding nucleic acid sequence, genomic sequences from which ASC cDNA can be transcribed, and/or allelic variants and homologues of the foregoing. The terms encompass double-stranded DNA, single-stranded DNA, and RNA.

As used herein, the term "inflammasome" means a multiprotein (e.g., at least two proteins) complex that activates caspase-1. The terms "NLRP1 inflammasome" and "NALP1 inflammasome" mean a protein complex of at least caspase-1 and one adaptor protein, e.g., ASC. For example, the terms "NLRP1 inflammasome" and "NALP1 inflammasome" can mean a multiprotein complex containing NLRP1, ASC, caspase-1, caspase-11, XIAP, and pannexin-1 for activation of caspase-1 and processing of interleukin-113, interleukin-18 and interleukin-33.

As used herein, the phrase "sequence identity" means the percentage of identical subunits at corresponding positions in two sequences (e.g., nucleic acid sequences, amino acid sequences) when the two sequences are aligned to maximize subunit matching, i.e., taking into account gaps and insertions. Sequence identity can be measured using sequence analysis software (e.g., Sequence Analysis Software Package from Accelrys CGC, San Diego, Calif.).

By the phrases "therapeutically effective amount" and "effective dosage" is meant an amount sufficient to produce a therapeutically (e.g., clinically) desirable result; the exact nature of the result will vary depending on the nature of the disorder being treated. For example, where the disorder to be treated is SCI, the result can be an improvement in motor skills and locomotor function, a decreased spinal cord lesion, etc. The compositions described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient" "subject" and "individual" are used interchangeably herein, and mean a mammalian subject to be treated, with human patients being preferred. In some cases, the methods of the invention find use in experimental animals, in veterinary applications, and in the development of animal models for disease, including, but not limited to, rodents including mice, rats, and hamsters, as well as primates.

As interchangeably used herein, "NALP1" and "NLRP1" mean an expression product of an NALP1 or NLRP1 gene or isoforms; or a protein that shares at least 65% (but preferably 75, 80, 85, 90, 95, 96, 97, 98, or 99%) amino acid sequence identity with NALP1 (e.g., accession number(s) AAH51787, NP001028225, NP127500, NP127499, NP127497, NP055737) and displays a functional activity of NALP1.

By the terms "stroke" and "ischemic stroke" is meant when blood flow is interrupted to part of the brain or spinal cord.

By "traumatic injury to the CNS" is meant any insult to the CNS from an external mechanical force, possibly leading to permanent or temporary impairments of CNS function.

The term "antibody" is meant to include polyclonal antibodies, monoclonal antibodies (mAbs), chimeric antibodies, humanized antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques. Such anti-ASC and anti-NLRP1 antibodies of the present invention are capable of binding portions of ASC and NLRP1, respectively, that interfere with caspase-1 activation.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 1A-D are photographs of immunoblots and graphs showing that SCI induces activation and processing of caspase-1 and increases levels of ASC and caspase-11 but not NALP1. FIGS. 1A-1B show representative immunoblot analysis of caspase-1 (A) and caspase-11 (B) in spinal cord lysates of SHAM (Sh) and traumatized rat cords at indicated times after injury. FIGS. 1C-1D show representative immunoblot analysis of ASC (C) and NALP1 (D) in spinal cord lysates of Sh and traumatized rat cords at indicated times after injury. FIG. 1C shows that anti-ASC reacts specifically with ASC (26 kDa) and nonspecifically with proteins of approximately 49 and 55 kDa (arrows, left). β-tubulin was used as internal standard and control for protein loading. Data are presented as mean±SEM. *$p<0.05$, *$p<0.10$ compared with sham. n=5 per group.

FIGS. 3A-3B are a photograph of an immunoblot and a micrograph showing that intraventricular injections of anti-NLRP1 antibody reduced the activation of caspase-1 and the processing of IL-1β. FIG. 3A is a representative immunoblot of caspase-1 and IL-1β on cortical lysates of mice treated with anti-NLRP1 or preimmnune serum control. β-Tubulin was used as a loading control. FIG. 3B shows that penetration of the antibody was confirmed by injection of anti-NLRP1 (chicken) intracerebroventricularly followed by processing for immunohistochemistry and labeling with anti-chicken-Alexa 594 conjugated antibody (red). Merged images of double-staining with NeuN (B, green) was used to determine the localization of the antibody in neurons. Scale bar=10 µm.

FIGS. 4A-4C are a series of photographs of immunoblots and graphs from a representative immunoblot analysis of NLRP1 (A), ASC (B) and caspase-1 (C) of cortical lysates of mice subjected to CCAT and sacrificed at different time points. Densitometric analysis shows that the active form of caspase-1 was significantly upregulated in the ipsilateral cortex of mice subjected to CCAT compared to sham animals. The adaptor protein ASC was also significantly upregulated at 7 d after ischemia when compared to the sham animals. NLRP1 did not significantly change at the time points tested. Densitometric values were normalized against β-tubulin. Data are mean+s.d. (N=5, *p<0.05).

FIG. 5A shows that treatment with anti-NLRP1 15 min after CCAT modestly reduced infarct areas at 3 bregma levels compared control animals. FIG. 5B shows that anti-NLRP1 treated CCAT mice consistently demonstrated reduced infarct volumes compared to control mice. Data are expressed as mean+s.e.m. (n=9-10/group)

DETAILED DESCRIPTION

Figure 2A:
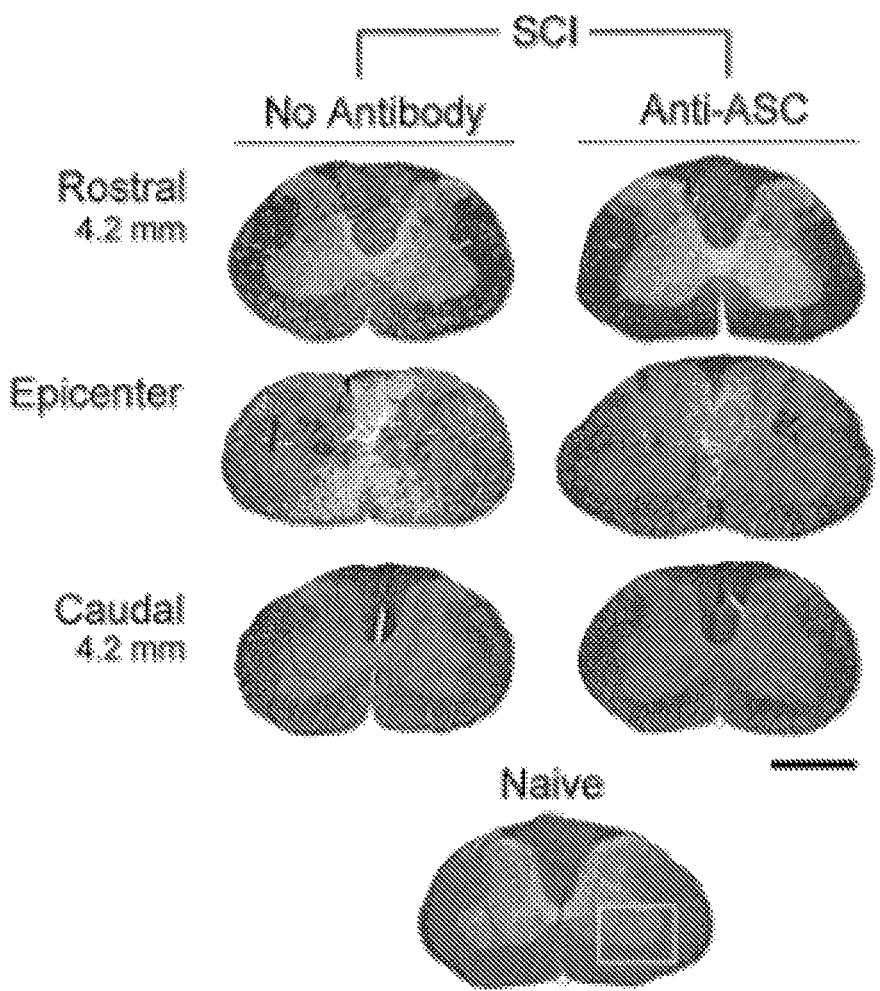
FIG. 2A is a series of images of representative cross sections of spinal cords of antibody-treated (anti-ASC) and nontreated animals (no antibody) at 3 d after SCI. Hematoxylin-eosin and luxol fast blue stained sections represent the injury epicenter and sites 4.2 mm rostral and caudal to the epicenter. Administration of anti-ASC significantly reduced the lesion volume at 3 d after injury. Areas of degeneration evaluated for volumetric analysis of the lesion were determined by diminished white matter degeneration and preservation of motor neuron morphology. Significance was determined by comparing average lesion volume of antibody-treated animals to control groups using Student's t-test. (N=5 per group). There were no differences between nontreated animals (no antibody) and IgG-treated controls.

The invention provides compositions and methods of reducing inflammation in the CNS of a mammal that has been subjected to a traumatic injury to the CNS, ischemic stroke, or having an autoimmune or CNS disease (e.g., ALS, Lou Gehrig's MS, immune dysfunction muscular CNS breakdown, MD, AD, PD). Based on the discoveries that: (1) ASC neutralization improves histopathological and functional outcomes in rats subjected to SCI; (2) ASC neutralization reduces caspase-1 activation and XIAP cleavage in rodents subjected to TBI; and (3) neutralization of NALP1 reduces cytokine activation and histopathological damage in mice subjected to thromboembolic (ischemic) stroke, the compositions and methods described herein include antibodies that specifically bind to at least one component (e.g., ASC, NALP1) of a mammalian inflammasome (e.g, the NALP1 inflammasome) and inhibit the activity of the at least one component, thereby inhibiting the processing of inflammatory caspases. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Immunology techniques are generally known in the art and are described in detail in methodology treatises such as Advances in Immunology, volume 93, ed. Frederick W. Alt, Academic Press, Burlington, Mass., 2007; Making and Using Antibodies: A Practical Handbook, eds. Gary C. Howard and Matthew R. Kaser, CRC Press, Boca Raton, Fla., 2006; Medical Immunology, $6^{th}$ ed., edited by Gabriel Virella, Informa Healthcare Press, London, England, 2007; and Harlow and Lane ANTIBODIES: A Laboratory Manual, Cold Spring Harbor Laboratory Press, Cold Spring Harbor, N.Y., 1988.

Reducing Inflammation in the CNS of a Mammal

Described herein are methods of reducing inflammation in the CNS of a mammal having a CNS injury or disease. In a typical method, the steps include: providing a therapeutically effective amount of a composition including an antibody that specifically binds to at least one component of a mammalian inflammasome (e.g, NALP1 inflammasome); and administering the composition to the mammal, wherein administering the composition to the mammal results in a reduction of caspase-1 activation in the CNS of the mammal. Examples of CNS injuries and diseases include SCI, TBI, stroke, and autoimmune or CNS disease (e.g., ALS, Lou Gehrig's MS, immune dysfunction muscular CNS breakdown, MD, AD, PD). The composition can be administered by any suitable route, e.g., intravenously, intraperitoneally, intracerebroventricularly. The composition can further include at least one pharmaceutically acceptable carrier or diluent.

In a typical embodiment, the antibody specifically binds to ASC or NALP1 (i.e., NLRP1). However, an antibody against any other component of a mammalian inflammasome (e.g., the NALP1 inflammasome) may be used. An antibody as described herein can be a monoclonal or polyclonal antibody.

In one embodiment, the CNS injury or disease is SCI, the mammalian inflammasome is the NALP1 inflammasome, and the at least one component of the NALP1 inflammasome is ASC. In this embodiment, administering the composition to the mammal results in an improvement in motor skills and locomotor function in the mammal as well as a decreased spinal cord lesion volume in the mammal. Any suitable antibody that specifically binds ASC can be used, e.g., an antibody that inhibits ASC activity in neurons of the mammal. In a typical embodiment, the antibody specifically binds to an amino acid sequence having at least 85% sequence identity with amino acid sequence SEQ ID NO:1 or SEQ ID NO:2. Similarly, in another embodiment, the CNS injury or disease is SCI, the inflammasome is the NALP1 inflammasome, and the at least one component is NALP1 (i.e., NLRP1). In this embodiment, the antibody specifically binds to an amino acid sequence having at least 85% sequence identity with amino acid sequence SEQ ID NO: 3 or SEQ ID NO: 4.

In another embodiment, the CNS injury or disease is ischemic stroke and the at least one component of the mammalian inflammasome (e.g., the NALP1 inflammasome) is NALP1 (NLRP1). Any suitable antibody that specifically binds to NALP1 can be used. In this embodiment, the composition can be administered intracerebroventricularly, intravenously, intraperitoneally, or any other suitable route. Administration of the composition results in a reduced infarct size in the mammal.

In a further embodiment, the CNS injury is a TBI and the at least one component of the mammalian inflammasome (e.g., the NALP1 inflammasome) is ASC. Alternatively, the at least one component of the inflammasome can be NALP1.

In the experiments described below, neutralization of ASC using an anti-ASC antibody and neutralization of NLRP1 using an anti-NLRP1 antibody reduced caspase-1 activation. However, the activity of any one of the NALP1 inflammosome components can be modulated (e.g., downregulated or inhibited) in a method of reducing inflammation in the CNS of a mammal that has been subjected to a traumatic injury to the CNS or that has a CNS disease.

Reducing Inflammation in the Brain of a Mammal Subjected to TBI

Described herein are methods of reducing inflammation in the brain of a mammal that has been subjected to a TBI. As described in the Examples below, traumatic injury promotes inflammation by activating caspase-1 in primary cortical neurons, the hippocampus and thalamus, inducing the processing of IL-1β in the cerebral cortex, and inducing expression of inflammasome proteins. It was discovered that anti-ASC antibody is taken up by cortical neurons and reduces TBI-induced activation and processing of caspase-1 and XIAP cleavage in vivo. Thus, a typical method of reducing inflammation in the brain of a mammal that has been subjected to a TBI includes the steps of providing a therapeutically effective amount of a composition including an antibody that specifically binds to ASC or NALP1; and administering the composition to the mammal such that the antibody is taken up by cells in the CNS (e.g., cortical neurons in the brain), wherein administering the composition to the mammal results in a reduction of caspase-1 activation and XIAP cleavage in the brain of the mammal. In a typical embodiment, the composition includes at least one pharmaceutically acceptable carrier or diluent and is administered intracerebroventricularly. The composition can be administered, however, by any suitable route, e.g., intravenously, intraperitoneally, etc.

Treating SCI in a Mammal

In the Examples below, rats subjected to SCI and subsequently treated with anti-ASC antibody showed an improved functional outcome (e.g., enhanced voluntary movement, improved posture and balance) and a decreased spinal cord lesion volume. Described herein are methods of treating SCI in a mammal (e.g., rodent, human). A typical method of treating SCI in a mammal includes the steps of providing a therapeutically effective amount of a composition including an antibody that specifically binds to ASC or NALP1; and administering the composition to the mammal such that the antibody is taken up by cells (e.g., spinal cord neurons) in the CNS, wherein administering the composition to the mammal results in an improvement in motor skills and locomotor function in the mammal. Administering the composition to the mammal can also result in a decreased spinal cord lesion volume in the mammal. Typically, the composition includes at least one pharmaceutically acceptable carrier or diluent (e.g., physiological saline or buffer) and is administered intravenously, intraperitoneally, or intracerebroventricularly.

Antibodies that Bind Specifically to at Least One Component of a Mammalian Inflammasome The methods described herein for reducing inflammation in the CNS (brain) of a mammal and treating SCI, TBI, and stroke in a mammal include compositions including an antibody that specifically binds to at least one component (e.g., ASC, NLRP1) of a mammalian inflammasome (e.g., the NALP1 inflammasome). A composition for treating SCI, TBI, stroke, autoimmune or CNS disease (e.g., ALS, Lou Gehrig's MS, immune dysfunction muscular CNS breakdown, MD, AD, PD) and/or reducing inflammation in the CNS of a mammal can further include at least one pharmaceutically acceptable carrier or diluent.

In one embodiment, a composition for treating SCI, TBI, stroke, and/or reducing inflammation in the CNS of a mammal includes an antibody that specifically binds to a region of rat ASC, e.g., amino acid sequence ALRQTQPYL-VTDLEQS (SEQ ID NO:1) (i.e., residues 178-193 of rat ASC, accession number BAC43754). In this embodiment, an antibody as described herein specifically binds to an amino acid sequence having at least 65% (e.g., 65, 70, 75, 80, 85%) sequence identity with amino acid sequence ALRQTQPYLVTDLEQS (SEQ ID NO:1) of rat ASC. In another embodiment, a composition for treating SCI, TBI, stroke, and/or reducing inflammation in the CNS of a mammal includes an antibody that specifically binds to a region of human ASC, e.g., amino acid sequence RESQ-SYLVEDLERS (SEQ ID NO:2). Such an antibody inhibits ASC activity in CNS cells, e.g., neurons, of a mammal.

In another embodiment, a composition for reducing inflammation in the brain of a mammal and treating ischemic stroke includes an antibody that specifically binds to NLRP1 (e.g., anti-NLRP1 chicken antibody). Any suitable anti-NLRP1 antibody can be used, and several are commercially available. In the experiments describe herein, a chicken anti-NLRP1 polyclonal that was custom-designed and produced by Ayes Laboratories was used. This antibody is directed against the following amino acid sequence in human NLRP1: CEYYTEIREREREKSEKGR (SEQ ID NO:3).

Anti-ASC and anti-NLRP1 antibodies as described herein include polyclonal and monoclonal rodent antibodies, polyclonal and monoclonal human antibodies, or any portions thereof, having at least one antigen binding region of an immunoglobulin variable region, which antibody specifically binds ASC or NLRP1. An antibody is specific for ASC if it is produced against an epitope of the polypeptide and binds to at least part of the natural or recombinant protein.

Methods for determining monoclonal antibody specificity and affinity by competitive inhibition can be found in Harlow, et al., Antibodies: A Laboratory Manual, Cold Spring Harbor Laboratory Press, Cold Spring Harbor, N.Y., 1988, Colligan et al., eds., Current Protocols in Immunology, Greene Publishing Assoc. and Wiley Interscience, N.Y., (1992, 1993), and Muller, Meth. Enzymol. 92:589-601, 1983, which references are entirely incorporated herein by reference.

Anti-ASC and anti-NLRP1 antibodies of the present invention can be routinely made according to methods such as, but not limited to inoculation of an appropriate animal with the polypeptide or an antigenic fragment, in vitro stimulation of lymphocyte populations, synthetic methods, hybridomas, and/or recombinant cells expressing nucleic acid encoding such anti-ASC or anti-NLRP1 antibodies. Immunization of an animal using purified recombinant ASC or peptide fragments thereof, e.g., residues 178-193 (SEQ ID NO:1) of rat ASC (e.g., accession number BAC43754) or SEQ ID NO:2 of human ASC, is an example of a method of preparing anti-ASC antibodies. Similarly, immunization of an animal using purified recombinant NLRP1 or peptide fragments thereof, e.g., residues MEE SQS KEE SNT EG-cys (SEQ ID NO:4) of rat NALP1 or SEQ ID NO:3 of human NALP1, is an example of a method of preparing anti-NLRP1 antibodies.

Monoclonal antibodies that specifically bind ASC or NLRP1 may be obtained by methods known to those skilled in the art. See, for example Kohler and Milstein, Nature 256:495-497, 1975; U.S. Pat. No. 4,376,110; Ausubel et al., eds., Current Protocols in Molecular Biology, Greene Publishing Assoc. and Wiley Interscience, N.Y., (1987, 1992); Harlow and Lane ANTIBODIES: A Laboratory Manual Cold Spring Harbor Laboratory Press, Cold Spring Harbor, N.Y., 1988; Colligan et al., eds., Current Protocols in Immunology, Greene Publishing Assoc. and Wiley Interscience, N.Y., (1992, 1993), the contents of which are incorporated entirely herein by reference. Such antibodies may be of any immunoglobulin class including IgG, IgM, IgE, IgA, GILD and any subclass thereof hybridoma producing a monoclonal antibody of the present invention may be cultivated in vitro, in situ or in vivo.

Administration of Compositions

The compositions of the invention may be administered to mammals (e.g., rodents, humans) in any suitable formulation. For example, anti-ASC antibodies and anti-NLRP1 antibodies may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to mammals by any conventional technique. Typically, such administration will be parenteral (e.g., intravenous, subcutaneous, intratumoral, intramuscular, intraperitoneal, or intrathecal introduction). The compositions may also be administered directly to a target site by, for example, surgical delivery to an internal or external target site, or by catheter to a site accessible by a blood vessel. When treating a mammal who has suffered from a stroke or TBI, the composition may be administered to the mammal intracerebroventricularly. The compositions may be administered in a single bolus, multiple injections, or by continuous infusion (e.g., intravenously, by peritoneal dialysis, pump infusion). For parenteral administration, the compositions are preferably formulated in a sterilized pyrogen-free form.

Effective Doses

The compositions described above are preferably administered to a mammal (e.g., a rat, human) in an effective amount, that is, an amount capable of producing a desirable result in a treated mammal (e.g., reducing inflammation in the CNS of a mammal subjected to a traumatic injury to the CNS or stroke or having an autoimmune or CNS disease). Such a therapeutically effective amount can be determined as described below.

Toxicity and therapeutic efficacy of the compositions utilized in methods of the invention can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an $ED_{50}$ with little or no toxicity. The dosage may vary within this range depending upon the dosage form employed and the route of administration utilized.

As is well known in the medical and veterinary arts, dosage for any one subject depends on many factors, including the subject's size, body surface area, age, the particular composition to be administered, time and route of administration, general health, and other drugs being administered concurrently.

EXAMPLES

The present invention is further illustrated by the following specific examples. The examples are provided for illustration only and should not be construed as limiting the scope of the invention in any way.

Example 1

SCI Activates the NALP1 Inflammasome and ASC Neutralization Improves Histopathological Outcome The inflammatory response initiated by SCI involves activation of interleukin-1β (IL-1β) that contributes to secondary cell death. In the peripheral immune response, the inflammasome activates caspase-1 to process proinflammatory cytokines, but the regulation of trauma-induced inflammation in the CNS has not heretofore been clearly understood. In the experiments described herein, it was shown that a molecular platform (termed the NALP1 inflammasome) including caspase-1, -11, ASC and NALP1 is expressed in neurons of the normal rat spinal cord, and forms a protein assembly with the inhibitor of apoptosis family member, XIAP. Moderate cervical contusive SCI induced processing of IL-1β, IL-18, activation of caspase-1, cleavage of XIAP, and promoted assembly of the multiprotein complex. Anti-ASC neutralizing antibodies administered to injured rats entered spinal cord neurons via a mechanism that was sensitive to carbenoxolone. Therapeutic neutralization of ASC reduced caspase-1 activation, XIAP cleavage, and interleukin processing, resulting in significant tissue sparing and functional improvement.

Materials and Methods

Adult female Fischer (180-200 g) rats were used in these studies. All animal procedures were approved by the Institutional Animal Care and Use Committee of the University of Miami. Rats were anesthetized with ketamine (87 mg/kg) and xylazine (13 mg/kg). Adequate amounts of anesthesia were determined by monitoring toe-touch. Using aseptic techniques, a midline incision was made in the neck in the skin and musculature to expose the C2-T1 vertebrae. A laminectomy was performed at vertebral level C5 exposing the cord. A moderate contusion injury (2,000 Kdyn of force) was induced by displacing the spinal cord 0.95 mm using the circular flap tip of the impactor of the Electromagnetic SCI Device (Ohio State University). Body and spinal cord temperature were maintained at 37.5° C. with a feedback-controlled heating blanket, which was monitored by a rectal thermometer. Following injury, the incision was closed with wound clips and sutures, and each rat was returned to its cage. Animals were sacrificed at different times following SCI. Sham animals were used as controls.

Rabbit anti-Rattus-novegicus ASC and NALP1 antisera were prepared by Bethyl Laboratories based on protein sequences (ASC=ALR QTQ PYL VTD LEQ S (SEQ ID NO:1); NALP1=MEE SQS KEE SNT EG-cys (SEQ ID NO:4)) obtained from the National Center For Biotechnology Information (NCBI) website: Accession number XP-340836 for NALP-1 and BAC43754 for ASC. Other antibodies were purchased from commercial sources and include: anti-NALP1 (abCam), anti-IL-1β (Cell Signaling), anti-IL-18 (R&D Systems), anti-caspase-1 (Upstate); anti-caspase-1 (Santa Cruz), anti-caspase-11 (Alexis Biochemicals), anti-caspase-11 (Santa Cruz), anti-XIAP (BD Transduction Laboratories); anti-caspase-3 (Upstate), anti-MAP2 (Chemicon), anti-APC (Chemicon), anti-GFAP (Chemicon), anti-CD11b (Chemicon), FITC-conjugated anti-actin (Sigma-Aldrich), Alexa Fluor 488-conjugated rabbit IgG (Invitrogen).

Neuronal cultures were prepared from E14-E15 rat embryo spinal cords as described (Tedeschi et al., J Cell Biol 102:2244-2253, 1986; and Keane et al., Transplantation 54:520-526, 1992). Spinal cord tissue was disrupted into a cell suspension by gentle trituration, and the cells were grown on poly-L-lysine-coated tissue culture dishes in N5 medium that contained 5% serum fraction. The neuronal nature of the majority of cells (95%) was confirmed electrophysiologically and immunohistochemically (Tedeschi et al., J Cell Biol 102:2244-2253, 1986). Cultures were grown for 14 d and then treated with 1.0 μM valinomycin (Sigma-Aldrich) for 4 h and controls were left untreated. Cells were washed once in ice-cold PBS, and lysed as previously described (Keane et al. J Neurosci Res 48:168-180, 1997). Supernatants were harvested and analyzed for IL-1β levels by ELISA (R&D Systems).

To investigate the mechanism by which spinal cord neurons uptake anti-ASC, spinal cord neurons were grown in culture for 7 d at a density of $2\times10^6$ per 60 mm tissue culture dish, and treated for 1 h with anti-ASC (5 μg) that was conjugated to FITC using the EZ-Label fluorescein isothiocyanate (FITC) Protein Labeling Kit (Thermos) according to the manufacturer's instructions. Other cultures were pretreated for 30 min with 10 mM cytochalasin D, to block endocytosis or with 100 μm carbenoxolone, a nonspecific pannexin inhibitor prior to addition of FITC-anti-ASC, FITC-actin or FITC-rabbit IgG alone. After 1 h incubation, neurons were washed twice in Dulbecco's phosphate buffered saline, fixed with 10% buffered formalin, and examined with a Nikon eclipse E600 fluorescent microscope.

Three- to four-mm segments of sham or injured spinal cords were homogenized in PTN50 extraction buffer (50 mM NaPi, pH: 7.4, 50 mM NaCl, 1% Triton X-100) with proteases (1 μg/ml pepstatin A, 1 μM aprotinin, 1 mM phenylmethylsulfonyl fluoride, 5 μg/ml leupeptin). Proteins were resolved in 10-20% Tris-HCl Criterion precasted gels (Bio-Rad), transferred to polyvinylidene difluoride membranes (Applied Biosystems) and placed in blocking buffer (PBS, 0.1% Tween-20, 0.4% I-Block (Applied Biosystems) and then incubated for 1 h with: monoclonal antibody to caspase-11 (1:1000, Alexis Biochemicals), monoclonal antibody to caspase-1 (1:1000, Upstate), rabbit anti-Rattus-novegicus, affinity purified antibody ASC (1:10,000, Bethyl Laboratories), NALP-1 (1:5000, Bethyl Laboratories), NALP-1 (1:1000, abCam). Membranes were incubated for 1 h with primary antibodies followed by appropriate secondary horseradish peroxidase (HRP)-linked antibodies (Cell Signaling). Visualization of signal was enhanced by chemiluminescence using a phototope-HRP detection kit (Cell Signaling). To control for protein loading, immunoblots were stripped with Restore, Western blot stripping buffer (Pierce) and blotted for β-tubulin using monoclonal anti-β-tubulin antibody (1:5000, BD Biosciences Pharmingen). Quantification of band density was performed using the NIH ImageJ 1.34s software, and data was normalized to β-tubulin.

To assess the protein composition and association of proteins in the inflammasome, 500 μg of spinal cord lysates from uninjured animals and traumatized animals at 30 min, 6 h and 3 d were immunoprecipitated with anti-ASC or anti-NALP1 antibodies using TrueBlot™ anti-Rabbit Ig immunoprecipitation beads. Spinal cord lysates were precleared by adding 50 μl of anti-rabbit TrueBlot™ beads to 500 μg of lysate in a microcentrifuge tube. The mixture was incubated for 1 h at 4° C., and beads were pelleted by centrifugation at 12,000×g for 30 sec. The supernatant was recovered and immunoprecipitated with 5 μg of anti-ASC or anti-NALP1 and incubated at 4° C. overnight. Fifty microliters of anti-rabbit TrueBlot™ beads were added to the mixture and incubated for 2 h and then centrifuged at 12,000×g for 30 sec. The pelleted beads were washed 5 times in lysis buffer, resuspended in loading buffer and heated at 95° C. for 3 min before analysis by immunoblotting using antibodies against ASC, NALP-1, capase-11 and caspase-1, caspase-3 and XIAP. Controls using pre-immune antiserum and a control reverse coimmunoprecipitation using anti-NALP1 were run in parallel. Anti-ASC and anti-NALP1 antibody specificity was evaluated by preabsorption of antiserum with immunogen peptides to remove specific antibody binding. Immunogen depleted antiserum was then used as a negative control for immunoblotting procedures.

Animals were anesthetized with ketamine (87 mg/kg) and xylazine (13 mg/kg) and perfused with 500 ml of 4% paraformaldehyde. Spinal cords were removed and placed in 4% paraformaldehyde at 4° C. for 20 h. Then cords were transferred to 20% sucrose in 0.1 M PBS and stored at 4° C. until sectioning.

Immunostained spinal cord sections of uninjured and injured rats at 6 h were examined with a Zeiss laser scanning confocal microscope (Zeiss, Inc.). Rats were perfused with 4% paraformaldehyde as described, and processed for cryostat sectioning (Leica SM 2000R Sliding Microtome). Sections (50 μm) were blocked by treatment with normal goat serum (Vector Laboratories). Tissue sections were rinsed with 0.1 M phosphate-buffered saline (PBS; pH 7.4) and incubated overnight at 4° C. with primary antibodies against caspase-1 (1:500), caspase-11 (1:500), ASC (1:500 dilution), and NALP-1 (1:500). To determine the precise cellular distribution of inflammasome proteins, sections were double stained with cell type specific markers: mouse anti-neuronal nuclei (NeuN, neurons—Chemicon); mouse anti-microtubule associated protein-2 (MAP2, neurons—Chemicon); mouse anti-APC (oligodendrocytes—CalBiochem); mouse anti-rat CD11b (microglia—Chemicon); and mouse anti-glial fibrillary acidic protein (GFAP, astrocytes—Chemicon). Alexa-Fluor secondary antibody conjugates (Molecular Probes) were used as secondary antibodies. Controls using an irrelevant antibody of the same isotype were run in parallel to evaluate antibody specificity. In addition, anti-ASC and anti-NALP1 antibody specificity was evaluated by preabsorption of antisera with immunogen peptides to remove specific antibody binding. Immunogen depleted antisera were then used as a negative control for immunostaining procedures. Sections were coverslipped with Vectashield mounting medium (Vector Laboratories) and analyzed with a Zeiss LSM510 laser scanning confocal microscope (Zeiss, Inc.).

Female Fischer rats were subjected to moderate cervical SCI. For inflammasome inhibition anti-ASC antibody (50 μg) was injected intravenously (i.v.) and intraperitoneally (i.p.) 20 min after SCI. Controls were treated with an equal amount of IgG, saline or were left untreated. After 24 h, animals were anesthetized with ketamine (87 mg/kg) and xylazine (13 mg/kg) and sacrificed. The spinal cord was immediately removed, frozen in liquid nitrogen, and preserved in a freezer at −80° C. until analysis by immunoblotting. For lesion volume analysis animals were treated for 2 additional days with 50 μg delivered i.p. Animals were then sacrificed 24 h after the last treatment. For behavioral testing animals were treated in a similar fashion but allowed to survive for 7 weeks after SCI. To test whether anti-ASC crossed the blood brain barrier, FITC-conjugated anti-ASC (50 μg) was administered (i.v. and i.p.) 20 min after SCI. FITC alone was used as a control. Animals were sacrificed 24 h later and processed for histology.

Spinal cord lysates were tested for caspase-1 protease activity using a caspase-1-specific peptide conjugated to a color or fluorescent reporter molecule (WEHD-AFC) (R&D Systems) according to the manufacturer's protocol.

For calculating areas and volumes of tissue atrophy and lesion volume following SCI, eleven coronal sections with easily identifiable anatomical landmarks were chosen for morphometric study. Quantification of lesion volume in the injured spinal cord was calculated. A 10-mm segment of spinal cord encompassing the injury site was fixed in paraformaldehyde (N=5 animals per group), transverse sectioned at 10 μm and then stained with hematoxylin, eosin, and luxol fast blue for gray and white matter visualization. Sections spaced at every 840 μm were used for analysis of injured white and gray matter using computer-assisted microscopy and Neuroleucida software (MicroBrightfield, Inc., Colchester, Vt.). In each section, the total area of the 10 mm-long cord segment was first determined. Damaged white and gray matter areas were determined. Tissue was characterized as damaged by the presence of infiltrating immune cells, myelin breakdown, shrunken eosinophilic neurons and hemorrhage. The areas of each section was calculated by Neuroleucida software and then summated for the volumes of each spinal cord.

A battery of tasks that have been proven useful in assessing functional outcome after cervical SCI were used for behavioral testing (Pearse et al., J Neurotrauma 22:680-702, 2005). These tests include the forelimb gripping strength test, the sticker removal test and footprint analysis.

To measure forelimb strength at 2 weeks after SCI, animals were gently held and permitted to grasp with their forelimbs a mesh grip connected to a digital force gauge (San Diego Instruments, San Diego, Calif.). The animal was then drawn along a straight line leading away, from the sensor until the animal released the mesh. The maximum grip stren10 was maintained and displayed (in Newtons) as the gripping force. The average reading of three successive trials was recorded for each animal.

Deficits in motor skills were examined by assessing the ability of rats to remove a sticker (1.0 inch diameter) that was placed in the bridge of their nose. A six-point rating scale was used to determine motor control (Diener and Bregman J Neurosci 18:763-778, 1998). Animals were allowed 2 min to remove the sticker and received a score of 1 to 6 based upon the following criteria: 1) animal did not attempt to remove the sticker; 2) animal attempted to remove the sticker but their forelimbs did not reach the sticker; 3) animal forelimbs reached the sticker after the head was contracted, but the sticker was not removed; 4) animal forelimbs reached the sticker without head contraction, but the sticker was not removed; 5) animal removed the sticker after several attempts; and 6) animals removed the sticker with no difficulty on the first attempt.

At 7 weeks after SCI, footprint analysis was used to quantify the ability of injured rats to maintain quadrupedal stance using the protocol of de Medinaceli et al. (Exp Neurol 77:634-643, 1982) with slight modifications. The animal's fore and hind paws were inked with different colors, and the animal was allowed to walk on a strip of paper covering a narrow runway measuring 1-m in length and 7 cm in width. A series of 8 sequential steps was used to determine the mean values of stride length, foot rotation, and base of support. Base of support was determined by measuring the core-to-core distance of the central pads of the forepaws. Stride length corresponded to the distance between consecutive steps with the forelimbs on each side. Foot rotation was defined by the angle formed by the third digit and the line through the central pad parallel to the walking direction.

Data are expressed as standard error of the mean (+/− s.e.m.). Statistical comparisons between uninjured and injured groups were made using two-tailed Student's t-test and a one-way ANOVA followed by Tukey's multiple comparison tests. P-values of significance used were *$P<0.05$, and #$P<0.10$.

Results

SCI induces processing of IL-1β and IL-18: Excessive levels of the proinflammatory cytokines IL-1β and IL-18 are associated with secondary damage following SCI. To determine whether SCI induced processing of proinflammatory cytokines, spinal cord lysates from injured and sham operated animals were analyzed for IL-1β and IL-18. Increased levels of pro-IL-1β and -IL-18 were present in spinal cord lysates within 15-30 min after injury. However, the time course of maturation of these inflammatory cytokines differed. Levels of IL-1β continued to rise early after injury, but decreased by 1 and 3 d post-trauma. In contrast, levels of processed IL-18 increased early after SCI, decreased by 3 h and then continued to rise by 1 and 3 d. Thus, SCI induces an inflammatory cascade consisting of production of pro-IL-1β, -IL-18, and processing of these precursors into mature inflammatory cytokines.

SCI induces expression of inflammasome proteins: Processing of pro-IL-1β and IL-18 involves the activation of a caspase-1-activating platform, termed the inflammasome (Martinon et al., Mol Cell 10:417-426, 2002; Martinon and Tschopp, 2006). In order to provide direct evidence for involvement of the inflammasome in SCI-induced inflammation, traumatized spinal cords were analyzed for the time course of expression of key inflammatory caspases and inflammasome proteins (FIG. 1). SCI rapidly activated caspase-1 (FIG. 1A) and upregulated caspase-11, the rodent ortholog of human caspase-5 (FIG. 1B). Proteolytic processing of procaspase-1 was detected at 15 min after trauma. Accordingly, there were significant increases in the levels of the adaptor protein ASC within 1 h after SCI (FIG. 1C), whereas no significant changes in the levels of NALP1 were observed (FIG. 1D). NALP3 was not detected in lysates from sham and traumatized animals at any time point examined and served as a control. These results demonstrate that SCI rapidly stimulates expression of inflammasome signaling molecules, suggesting involvement of the inflammasome in the initiation of the inflammatory response following SCI.

SCI induces dramatic changes in the composition of the inflammasome multiprotein complex: In humans, three types of inflammasomes have been proposed based on biochemical analysis of three-Apaf-like proteins, NALP1, NALP2/3 and Ipaf (Tschopp et al., Nat Rev Mol Cell Biol 4:95-104, 2003; Agostini et al., Immunity 20:319-325, 2004; Dinarello et al., Immunity 20:243-244, 2004). However, the protein composition of inflammasomes in the rat has not yet been established. To characterize associations of inflammasome proteins after SCI, coimmunoprecipitations of spinal cord lysates from sham (uninjured) rats and lysates at various time points after injury were performed using anti-ASC antibody. In sham spinal cords, ASC was immunoprecipitated with anti-ASC; however very low levels of caspase-1 and -11 were present in this signaling complex. NALP1 was associated with ASC in sham spinal cords, whereas high levels of full-length XIAP were present in the multiprotein complex. At 30 min after SCI, the composition of the signaling complex changed. Notably, there was increased association of caspase-1 and caspase-11 with ASC, but the levels of NALP1 associated with ASC remained constant. However, the levels of full-length XIAP in the molecular platform decreased. The cleaved p26 and p13 subunits of caspase-1 were generated at 30 min after SCI. At 6 h and 3 d after trauma, the full-length 53-kDa XIAP protein was cleaved to generate 25- and 30-kDa fragments. Anti-ASC did not immunoprecipitate caspase-3, whereas preimmune serum did not immunoprecipitate the inflammasome-associated proteins, demonstrating antibody specificity, and thus serving as controls. In reciprocal coimmunoprecipitation experiments, anti-NALP1 immunoprecipitated ASC, caspase-1, and -11, as well as XIAP, but it did not immunoprecipitate caspase-3, thus providing additional evidence for formation of the inflammasome complex after SCI. These findings suggest that SCI activates a molecular platform (termed the NALP1 inflammasome) that consists of ASC, caspase-1, caspase-11, NALP1 and XIAP leading to activation of caspase-1 and cleavage of XIAP.

Inflammasome proteins are present in spinal cord neurons, and SCI induces alterations in protein expression pattern: Confocal images of the cell type expression and regional distribution of NALP1 inflammasome proteins in motor neurons in the ventral horn of sham and injured spinal cords at 6 h after injury were obtained. Sections were stained for caspase-1, caspase-11, ASC and NALP1, and the neuronal marker MAP2. Caspase-1 immunoreactivity was seen in MAP2 positive cells, indicating that caspase-1 is expressed in neurons in the spinal cord of sham animals. Intense caspase-1 immunoreactivity was seen in the nucleus, and patchy staining was present in the cell cytoplasm and processes. In contrast, caspase-11 immunoreactivity demonstrated diffuse punctate staining confined to the neuronal soma and processes. Intense ASC and NALP1 staining was detected in the soma of spinal cord neurons and exhibited a patchy distribution pattern, while weak NALP1 immunoreactivity was detected in the nucleus. Astrocytes, oligodendrocytes and microglia expressed ASC but did not express NALP1, suggesting that ASC may serve as an adaptor for the enhancement of other inflammasome complexes (NALP2/3) in glial cells.

Moderate cervical SCI resulted in altered staining patterns of inflammasome proteins in spinal cord neurons. At 6 h after injury, increased caspase-1 immunoreactivity was present in neuronal nuclei, while intense caspase-1 staining was seen in the cell cytoplasm as large patches near the plasma membrane. Increased caspase-11 staining was present in the neuronal soma that was localized in a patchy distribution. A more striking alteration was observed in the immunostaining of ASC and NALP1 after SCI. By 6 h after SCI, immunoreactivity of both inflammasome proteins was markedly enhanced, and intense patchy staining was seen in the neuronal soma near or associated with the plasma membrane. XIAP was present in the perinuclear region and cell processes of spinal cord neurons and SCI induced alterations in the expression pattern. The cellular distribution and location of NALP1 inflammasome proteins near the plasma membrane of neurons after SCI is consistent with their role in the processing and secretion of IL-1 ft Anti-ASC and anti-NALP1 antibody specificity was evaluated by preabsorption of antiserum with immunogen peptides to remove specific antibody binding. Immunopeptide depleted antiserum did not stain sections of sham and traumatized spinal cords and served as a negative control. Of importance is the fact that the intensity and pattern of inflammasome protein expression in neurons was strikingly altered by SCI and is consistent with the idea that neurons process and secrete IL-1β and IL-18 via activation of the inflammasome complex.

To further confirm that inflammasome proteins formed protein/protein interactions in neurons, triple immunohistochemical labeling was performed followed by confocal microscopy. Caspase-1, ASC and NALP1 were present in motor neurons of the spinal cord, and demonstrated overlapping expression patterns as evidenced in the profile analysis. Similar overlapping staining patterns were observed in sections stained with caspase-11, ASC and XIAP, supporting the idea that caspase-1, -11, ASC, NALP1 and XIAP form a multiprotein complex within the cytoplasm of motor neurons of the spinal cord. These immunohistochemical studies support coimmunoprecipitation experiments that show protein/protein interactions among ASC/ caspase-1/caspase-11/NALP1 and XIAP and immunohistochemical data, demonstrating colocalization of these proteins in neurons.

Spinal cord neurons in culture express NALP1 inflammasome proteins and valinomycin treatment activates the inflammasome: Spinal cord neurons grown in culture were assayed for expression of inflammasome components. Spinal cord neurons expressed NALP1, ASC, caspase-1, caspase-11 and XIAP, but the relative proportions of these components in cultured neurons differed from those expressed in spinal cord tissue. To test whether $K^+$-efflux is required for NALP1 inflammasome activation, spinal cord neurons were treated with the $K^+$ ionophore valinomycin. Valinomycin triggered activation and processing of caspase-1 and resulted in a significant increase of IL-1β (38.72±3.43 pg/ml) in the culture medium when compared to untreated neurons (24.24±0.80 pg/ml). Thus, activation of the NALP1 inflammasome and release of IL-1β in spinal cord neurons is dependent on $K^+$ efflux.

ASC neutralization reduces SCI-induced activation and processing of caspase-1, IL-1β, IL-18, and XIAP cleavage: The blood-spinal cord barrier is intact before injury and becomes disrupted by the insult. Since motor neurons have the ability to uptake IgG (Mohamed et al., 2002), it was determined whether anti-ASC was taken up by spinal cord neurons in vivo. Anti-ASC-conjugated-FITC or FITC alone (control) was administered at 20 min after SCI, and the injured spinal cord was excised 24 h later. Cords were sectioned and examined by confocal microscopy. Large spinal cord motor neurons stained with FITC-conjugated anti-ASC, whereas FITC administration alone did not label spinal cord neurons. To investigate the mechanism by which the spinal cord incorporates anti-ASC, spinal cord neurons were grown in culture for 7 d. Neurons were treated with cytochalasin D (endocytosis inhibitor) or carbenoxolone (nonspecific pannexin inhibitor) and then incubated with FITC-conjugated anti-ASC, FITC-conjugated actin or FITC alone. Spinal cord neurons incorporated FITC-conjugated anti-ASC, whereas FITC-conjugated actin was excluded from these cells. Moreover, anti-ASC uptake was abolished by pretreatment with carbenoxolone, but was not inhibited by cytochalasin D. Thus, it appears that uptake of anti-ASC by spinal cord neurons is sensitive to carbenoxolone treatment.

To dissect the contribution of the NALP1 inflammasome to SCI-induced inflammation, the activity of the NALP1 inflammasome was blocked with antibodies against the inflammasome adaptor protein ASC. Antibody treatment was started 20 min after trauma. One group of animals received an intravenous (i.v., 50 μg) and an intraperitoneal (i.p., 50 μg) injection of ASC neutralizing antibody. These two routes of antibody delivery were chosen to minimize inflammasome activation systemically and in the CNS. Control groups received saline alone, remained untreated or received IgG of the same isotype corresponding to anti-ASC.

Spinal cords were removed at 24 h after treatment and lysates were prepared and immunoblotted for caspase-1, IL-1β, IL-18 and XIAP. Neutralization of ASC significantly reduced activation and processing of IL-1β, IL-18, and caspase-1, and decreased XIAP cleavage. Levels of other proteins comprising the NALP1 complex did not change following antibody neutralization. Moreover, spinal cord lysates were tested for caspase-1 protease activity using a caspase-1-specific peptide conjugated to a fluorescent reporter molecule WEHD-AFC. Treatment with ASC neutralizing antibody significantly reduced caspase-1 activity (42%) compared to sham animals, indicating that this treatment strategy significantly decreases activation of one of the key components in inflammasome signaling following trauma to the spinal cord. Thus, ASC neutralization interferes with inflammasome signaling pathways of caspase-1 activation and processing of inflammatory cytokines induced by SCI.

Figure 2B:
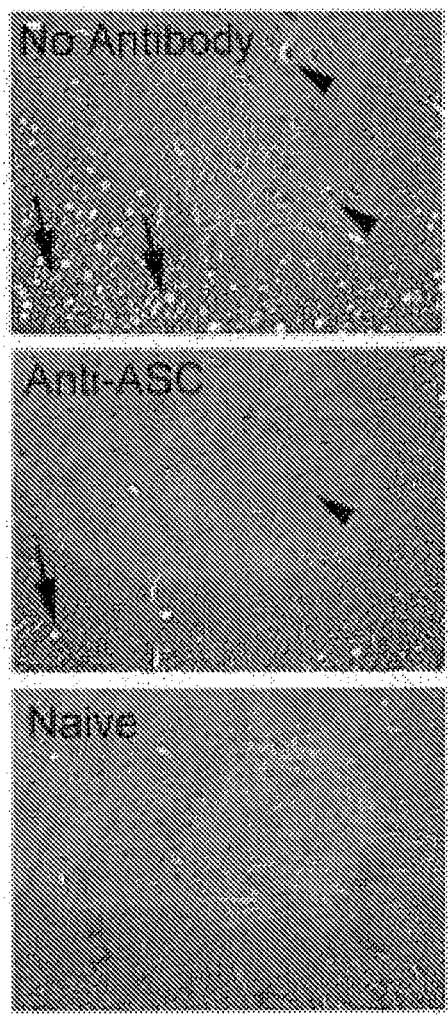
FIG. 2B shows that spinal cords from animals treated with anti-ASC demonstrated fewer shrunken neurons in gray matter (arrowheads) and reduced white matter degeneration (arrows).
Figure 2C:
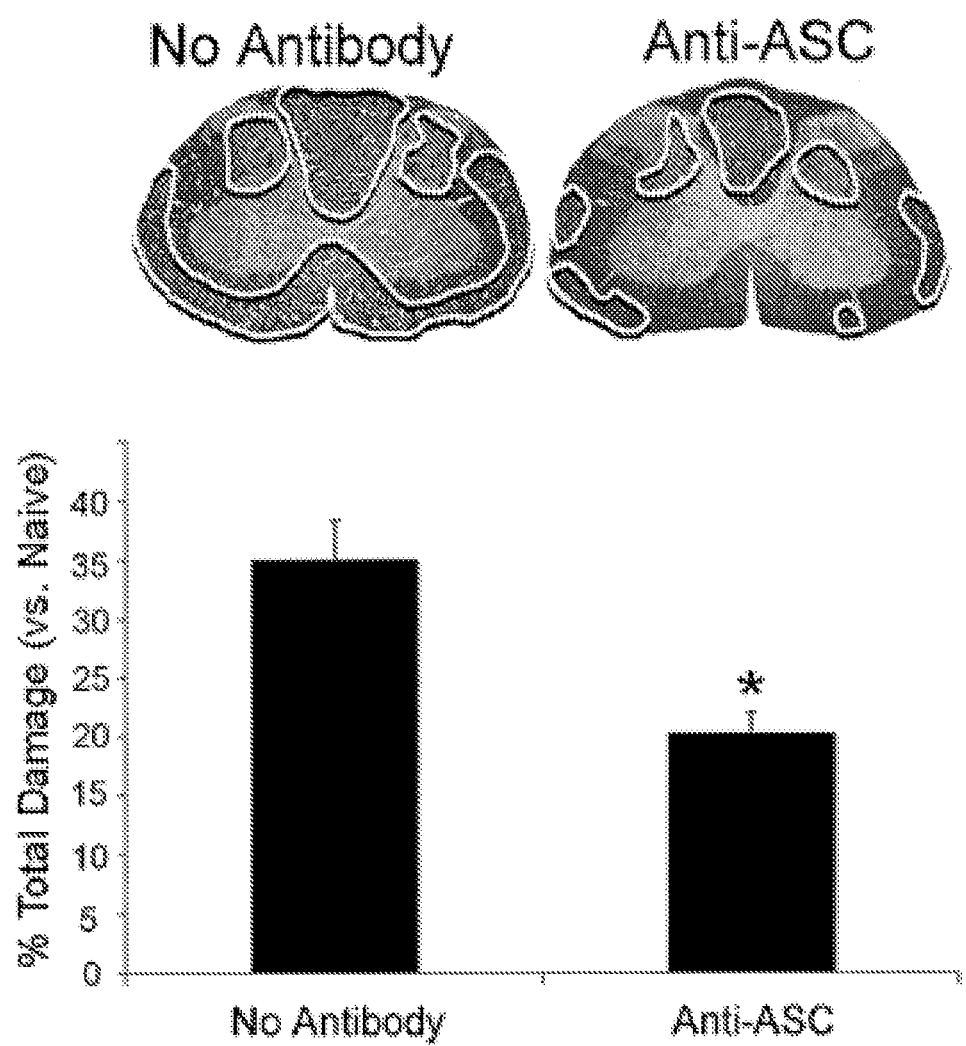
FIG. 2C shows that administration of anti-ASC significantly reduced the lesion volume at 3 days after injury. Areas of degeneration evaluated for volumetric analysis are outlined. Significance was determined by comparing average lesion volume of antibody-treated animals to naïve groups using Student's t-test (N=5 per group). Data are presented as mean±s.e.m. *p<0.05 compared to non-treated animals. Scale bar, 50 µm.

ASC neutralization decreases spinal cord lesion volume: To determine whether inflammasome signaling was causally linked to tissue damage during SCI in vivo, the activity of ASC was blocked with neutralizing antibodies and the lesion volumes were measured at 3 d after injury. Rats were subjected to cervical SCI and then treated with anti-ASC antibody. Other groups of rats were left untreated (no antibody) or treated with IgG and served as controls. FIG. 2A shows representative spinal cord sections of the lesion epicenter, and areas rostral and caudal to the impact site at 3 d after trauma. Spinal cords from animals treated with anti-ASC demonstrated smaller areas containing shrunken eosinophilic neurons in gray matter (FIG. 2B, arrow heads) and reduced white matter degeneration (FIG. 2B, arrows). Importantly, administration of anti-ASC antibody significantly reduced (43%) the lesion volume as determined by diminished white matter degeneration and preservation of motor neuron morphology (FIG. 2C).

ASC neutralization improves functional outcomes after SCI: To investigate the long-term consequences of neutralization of ASC, tests were conducted that reflected the integrity of dorsal spinal motor tracts (cortico- or rubrospinal). The grip strength test directly measures the force with which the rat grasps objects and reflects the loss of motorneurons at C5-C6 of the spinal cord. Rats were treated with neutralizing antibodies to ASC, with IgG or left untreated as controls. Only rats exhibiting a significant improvement in grip strength were those treated with neutralizing antibodies. Deficits in descending motor control were examined by assessing the ability of the rat to remove a sticker placed on their nose-bridge (Diener and Bregman J Neurosci 18:763-778, 1998). Again, only rats treated with anti-ASC antibody showed a significant recovery of voluntary movement compared with control rats. Footprint analysis was conducted to examine motor coordination and evaluate foot placement and stance during locomotion. Animals treated with neutralizing antibodies had significant improvements in base of support and foot rotation, but there was no significant improvement in stride length. Thus, ASC neutralization enhances voluntary movement and improves posture and balance after cervical SCI.

Example 2

Inhibition of the Inflammasome Complex Reduces the Inflammatory Response after Thromboembolic Stroke in Mice The purpose of the experiments described herein was to determine whether the molecular platform NLRP1 (NLR (nucleotide binding, leucine-rich repeat), pyrin domain containing 1), composed of capase-1, ASC (apoptosis-associated speck-like protein containing a caspase-activating recruitment domain) and NLRP1, is expressed in the normal and postischemic brain. Mice underwent thromboembolic stroke to investigate the formation of the inflammasome and subsequent activation of downstream inflammatory responses. Western blot analysis demonstrated expression and activation of interleukin (IL) IL-β and IL-18 at 24 hrs after stroke. Size-exclusion chromatography and co-immunoprecipitation analysis showed protein association between NLRP1, ASC and caspase-1. As early as 24 hrs after ischemia, immunohistochemical analysis revealed inflammasome proteins in neurons, astrocytes, microglia and macrophages. The therapeutic potential of the inflammasome as an anti-inflammatory target was demonstrated by reduced cytokine activation and reduced histopathological damage in mice treated after ischemia with a neutralizing antibody against NLRP1. These findings show that the inflammasome complex forms in the brain after focal ischemia and may be a novel therapeutic target for reducing the detrimental consequences of post-ischemic inflammation.

Material and Methods

Male mice (C57BL/6J, USA, Charles Rivers Laboratories) weighing 19-25 g and 12-16 weeks old were used in this study. Mice were provided with a standard diet and tap water ad libitum. All animal procedures followed the National Institutes of Health Guide for the Care and Use of Laboratory Animals and were approved by the University of Miami's Animal Care and Use Committee.

Common carotid artery thrombosis (CCAT) was performed as described by Lozano and colleagues (2007). Briefly, mice were anesthetized and a 32-gauge catheter connected to an infusion pump (PHD2000, Harvard) was inserted into the left femoral vein. The right common carotid artery (CCA) was dissected by blunt technique and the external carotid artery (ECA) was ligated. Total occlusion of the CCA was obtained by photoactivation of Erythrosin B 190449 (ICN Biomedicals Inc). Mice were perfused with Erythrosin B (35 mg/kg) via the femoral vein at a rate of 17.5 mg/kg per minute. Simultaneously, a tunable argon laser (Innova 70-4, Coherent) was focused onto the right CCA and the artery was irradiated for 10 minutes. Local vascular thrombosis and subsequent occlusion of the CCA was verified with a Transonic Doppler flow probe (Model 0.5 VB, Transonic Systems, Ithaca, N.Y.) coupled with a temperature probe placed on the distal right CCA. Sham-operated animals were performed by perfusion with Erythrosin B but laser irradiation was omitted to avoid activation of the dye. In a separate series of CCAT mice, physiological variables were assessed including arterial blood pressure, $PCO_2$, $PO_2$ and pH. These values were found to be within normal ranges as previously described (Lozano et al., J Neurosci Methods 162:244-254, 2007).

At various times after CCAT, brains were removed and placed on ice. Regions of the right cerebral cortex corresponding to the middle cerebral artery (MCA) territory were dissected in a glass Petri dish on ice and stored at −80° C. The tissue was homogenized using a Dounce homogenizer (35 strokes) in 1.5 ml of lysis buffer: 15 mM HEPES pH 7.6, 0.25 M sucrose, 1 mM $MgCl_2$, 2.5 mM EDTA, 1 mM EGTA, 1 mM DTT, and 1× protease inhibitor cocktail set I (Calbiochem, La Jolla, Calif., USA). Samples were assayed for total protein using the Coomassie Assay kit (Bio-Rad Laboratories, Hercules, Calif., USA). Samples were then heated with 1× sample buffer and stored at −80° C.

Equal amount of proteins (25 µg) were electrophoresed on denaturing polyacrylamide gels (BioRad precasted 10-20% SDS-PAGE) and transferred by standard electroblotting techniques to a polyvinylidene difluoride (PVDF) membrane (Immobilon PVDF, Millipore), blocked with Tween 20 (0.1%) and incubated overnight at 4° C. with the following antibodies: mouse anti-caspase-1 monoclonal and rat anti-mouse ASC monoclonal were kindly provided by Dr. Mariathasan (Genetech, CA). Chicken anti-NLRP1 polyclonal was custom-designed and produced by Ayes Laboratories (Sequence: CZYYTEIREREREKSEKGR (SEQ ID NO:3)). Mouse anti-IL-18 monoclonal was purchased from R&D Systems (Mab521, Minneapolis, Minn.). Rabbit anti-cleaved IL-1β polyclonal (Asp116) and secondary antibodies HRP-conjugated were obtained from Cell Signaling (Danvers, Mass.). Visualization of the signal was performed by enhanced chemiluminescence (Amersham Biosciences, Piscataway, N.J., USA). Quantification of bands was made by scanned densitometric analysis and Labwork 4.0 image analysis (UVP Bioimaging System).

Dissected ipsilateral cerebral cortices corresponding to the MCA territory were homogenized with the following protein extraction buffer: 20 mM HEPES-KOH [pH 7.5], 10 mM KCl, 1.5 mM $MgCl_2$, 1 mM Na EDTA, 1 mM Na EGTA, and 1× protease inhibitor cocktail set I (Calbiochem, La Jolla, Calif., USA). Samples were then centrifuged at 18000×g for 10 min at 4° C. and run on a Superose 6 size-exclusion chromatography column. Two hundred microliter-fractions were collected starting at the void volume time. Fractions were pooled (n=3) and proteins were concentrated with trichloroacetic acid (80 µl) at 4° C. for 1 hr. After centrifugation, samples were then washed with acetone and resuspended in 1× sample buffer, heated at 95° C. for 5 min and resolved in SDS-PAGE gels followed by immunoblot analysis. Protein standards were run on a column under identical conditions and analysis of the fractions was performed by absorbance at 280 nm.

Fractions corresponding to the high molecular weight (>600 kDa) proteins in the size-exclusion chromatography analysis were pooled for coimmunoprecipitation studies (fractions 6 to 15, 2 ml total volume). Samples were pre-cleared with the protein G-sepharose immunobeads (Amersham Bioscience) and then incubated with the monoclonal antibody anti-ASC overnight at 4° C. Protein G-Sepharose immunobeads were added to the mixture and incubated for 2 hr and then centrifuged at 12,000×g for 30 sec. The pelleted beads were washed 5 times in lysis buffer, resuspended in loading buffer and heated at 95° C. for 3 min before analysis by immunoblotting Mice were anesthetized and perfusion-fixed with 4% paraformaldehyde for immunohistochemical analysis. Coronal floating sections (60 µm) were cut with a microtome and immunostained with the following antibodies using procedures previously established (Keane et al., J Cereb Blood Flow Metab 21:1189-98, 2001). Rabbit polyclonal anti-caspase-1 (1:1000) was obtained from Millipore (Charlottesville, Va.) while cell markers such as anti-GFAP and anti-NeuN were purchased from Chemicon. Secondary antibodies conjugated to Alexa-fluorochromes were obtained from Molecular Probes-Invitrogen (Carlsbad, Calif.). Additionally, sections were treated with Sudan black 0.3% in 70% ethanol to quench the auto-fluorescence produced by the injured tissue. Images were obtained with a LSM510 laser confocal microscope (Carl Zeiss, Inc., Thornmood, N.Y., USA). At least 3 different sections were prepared from each animal; all animals in each group yielded similar results. Control labeling included omission of primary antibodies and labeling with pre-immune serum and auto-fluorescence controls omitted the use of primary and secondary antibodies.

Mice were subjected to CCAT as previously described. Fifteen minutes following CCAT, animals were placed in prone position and injected stereotactically into the right lateral ventricle with 5 µg of anti-NLRP1 chicken antibody. Control mice were injected with the same amount of pre-immune chicken serum under identical conditions. For immunoblot analysis of caspase 1 and IL-1β, treated and control treated mice (n=5/group) were sacrificed 24 hr after treatment and brains were rapidly removed. Right cortices corresponding to the MCA territory were dissected and stored at −80° C. Samples were processed for immunoblot analysis as previously described.

For histopathological analysis of treated (n=9) and non-treated (n=10) mice, another group of animals was anesthetized and perfusion-fixed with formaldehyde-acetic acid-methanol (FAM) at 24 hr following CCAT. Brains were removed and immersion-fixed for 2 d in fixative. Ten micron coronal sections were next stained with hematoxylin and eosin (H&E) and infarct volumes were analyzed using Neurolucida Investigator software. Brains were analyzed from bregma levels +1.70, +1.0, 0.0, −0.4 and −1.22 to maintain homogeneity during the assessment process. For calculating areas of infarction following CCAT, coronal sections from 5 bregma levels with easily identifiable anatomical landmarks were chosen for morphometric study (Dietrich et al., Stroke 30:855-62, 1999). Tissue was characterized as damaged by the presence of disrupted neuropil, shrunken eosinophilic neurons and hemorrhage. Quantification of infarct volume in the damaged brain was then calculated by Neurolucida software based on the integration of the various infarct areas.

Statistical comparisons for infarct volume and areas between uninjured and injured groups were made using Student's t-test and repeated measures ANOVA, respectively. Immunoblot data were analyzed using Kruskal-Wallis statistical test. Biochemical data are presented as mean±s.d. Histological data are presented as mean+s.e.m. P-value of significance was *P<0.05.

Results

Thromboembolic stroke induces processing of IL-1β and IL-18: The proinflammatory cytokines IL-1β and IL-18 are the downstream effectors of activated caspase-1 and directly mediate the inflammatory response (Martinon and Tschopp, Cell 117:561-74, 2004). First, the expression and activation of IL-1β and IL-18 after thromboembolic stroke were characterized using specific antibodies against the pro- and active forms of IL-1β and IL-18. Increased levels of pro- and active IL-1β and IL-18 were present in lysates of infarcted tissue at 24 hr and remained elevated until 7 d post-ischemia, and then decreased thereafter. Thus, the active forms of these inflammatory cytokines were increased acutely after ischemia and remained elevated during the first week post CCAT.

CCAT induces expression of inflammasome proteins: To investigate the profile of protein expression involved in the formation of the inflammasome complex, immunoblot analysis was performed on mice subjected to CCAT at different time points following ischemic insult (FIG. 4). Caspase-1 activation, as detected by the presence of the cleaved 26-kDa fragment, was increased at 3 d after CCAT. Seven days after ischemia, the adaptor protein ASC was also significantly increased. NLRP1 expression did not increase following ischemia as determined by densitometric analysis of immunoblots that showed no statistically significant difference when compared to sham-operated animals. These results demonstrate that CCAT stimulates the expression of inflammasome signaling molecules, suggesting a possible involvement of the inflammasome in the initiation of inflammation following thromboembolic stroke.

CCAT induces formation of the NLRP1 inflammasome complex: The assembly of the inflammasome proteins into the complex was next analyzed by size-exclusion chromatography in animals 24 hrs after CCAT. Immunoblots were run on collected fractions and probed for caspase-1, ASC and NLRP1. NLRP1, ASC and caspase-1 were present in the non-associated low molecular weight fractions. The specific bands for caspase-1, as well as NLRP1 and ASC were also detected in fractions corresponding to high molecular weight proteins (>600 kDa) termed the inflammasome fractions. Elution profile of caspase-6 was used as a control and showed that this protein was not present in the multiprotein complex in the inflammasome fractions. These data suggest that the NLRP1 inflammasome complex consisting of ASC, caspase-1 and NLRP1 forms in the brain after a thromboembolic ischemic insult.

Figure 4C:
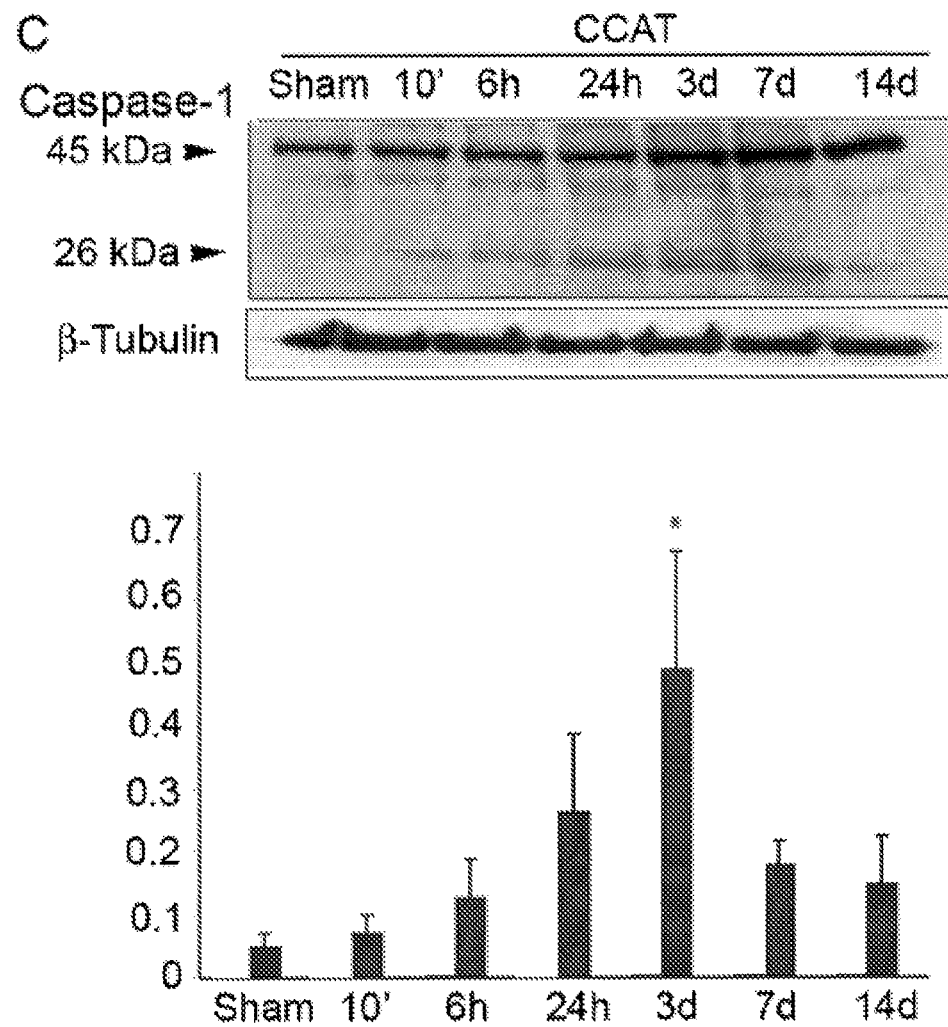

Association of inflammasome proteins was confirmed by coimmunoprecipitation experiments of brain proteins lysates from mice subjected to CCAT and sacrificed 24 hrs later (FIG. 4C). Pooled fractions corresponding to the inflammasome molecular weight (>600 kDa) obtained by size-exclusion chromatography were immunoprecipitated with anti-ASC. Immunoprecipitates were blotted for ASC, caspase-1, and NLRP1. Anti-ASC immunoprecipitated ASC, NLRP1, and caspase-1. Normal rat IgG2 did not immunoprecipitate the inflammasome-associated proteins and was utilized as a control, demonstrating antibody specificity.

NLRP1 inflammasome proteins are present in neurons, astrocytes and microglia/macrophages: To determine the cell-type expression pattern of inflammasome proteins, immunohistochemical analysis was performed using triple labeling for caspase-1, NLRP1 and ASC on brain sections of animals sacrificed 24 hrs after CCAT. Caspase-1, NLRP1 and ASC were present in cells surrounding the infarcted cortex. Based on morphological criteria, these cells appear to be microglia/macrophages, but other cells, probably astrocytes or neurons were also immunoreactive for caspase-1 and NLRP1. Although some inflammasome proteins were found in the nucleus, profile analysis showed that colocalization signals were present in the cytoplasm of cells.

To determine whether other CNS cells express inflammasome proteins within the brain, immunohistochemical labeling was performed on normal/sham mouse brains and in animals subject to CCAT and sacrificed at several survival periods (6 hrs, 24 hrs and 7 d). Sections were double-labeled for the inflammasome proteins NLRP1, ASC and caspase-1 and the cell markers NeuN (neurons), glial fibrillary acidic protein (GFAP, astrocytes) and lectin (microglia/macrophages). Table 1 summarizes the cell type expression patterns on inflammasome proteins in sham and injured animals. At 24 hrs and 7 d following CCAT, caspase-1, NLRP1 and ASC were detected in microglia and macrophages located within the core and periphery of the infarcted cerebral cortex. Caspase-1 and NLRP1 immunoreactivity was not detected in microglia in normal brain sections. However, caspase-1 staining was detected in cortical neurons of sham animals in the cytoplasm and the nucleus. At 6 to 24 hrs after ischemia, caspase-1 and NLRP1 immunoreactivity dramatically increased in the cytoplasm of neurons located in intact regions surrounding the infarcted cortex. ASC was expressed in both naïve and ischemic cortical neurons (Table 1). Finally, GFAP-positive astrocytes were also immunoreactive for NLRP1 in the normal brain, and caspase-1 and ASC were only detected following the thromboembolic ischemic event in some astrocytes surrounding the infarct at 7 d post-CCAT (Table 1). These findings together with the size exclusion chromatography results suggest that CCAT triggers formation of the NLRP1 inflammasome in neurons, microglia/macrophages and astrocytes.

TABLE 1

Summary of Cellular Localization of Inflammasome Proteins in the Ischemic Brain

|  | Naïve | 6 hr | 24 hr | 7 days |
|---|---|---|---|---|
| Caspase-1 | | | | |
| Neurons | + | + | + | + |
| Astrocytes | − | + | + | + |
| Microglia/macrophages | − | − | + | + |
| NLRP1 | | | | |
| Neurons | + | + | + | + |
| Astrocytes | + | + | + | + |
| Microglia/macrophages | − | + | + | + |
| ASC | | | | |
| Neurons | + | + | + | + |
| Astrocytes | − | − | − | + |
| Microglia/macrophages | + | + | + | + |

NLRP1 neutralization reduces CCAT-induced activation and processing of caspase-1: To determine whether inhibition of the inflammasome complex reduces the inflammatory response after CCAT, mice were injected intracerebroventricularly with a chicken polyclonal antibody against NLRP1 15 min following CCAT. Animals were then sacrificed at 24 hrs (n=5) and processed for immunoblotting for caspase-1 and IL-1β. Preimmune serum was injected in a different group of animals as a control (n=5). Immunoblotting for caspase-1 and cleaved IL-1β showed that anti-NLRP1 reduced the levels of active caspase-1 whereas animals treated with preimmune serum or IgG showed elevated levels of caspase-1 and IL-1 (FIG. 3A).

To determine whether anti-NLRP1 crossed the BBB, anti-NLRP1 was injected into the right lateral ventricle 15 minutes after CCAT and brains were processed for immunohistochemical analysis. Sections were then immunobeled with anti-chicken-Alexa conjugated antibody to detect the chicken NLRP1 antibody. Double labeling with NeuN or GFAP antibodies were used to determine which CNS cells reacted with anti-NLRP1. Preimmune serum was used as a control. FIG. 3B shows a confocal image of cortical brain tissue with anti-chicken-Alexafluor 594 conjugated NAPL1 antibody and NeuN double staining The injected anti-NLRP1 antibody was detected in neurons and activated astrocytes in brain regions within the ipsilateral cerebral cortex.

Figure 5A:
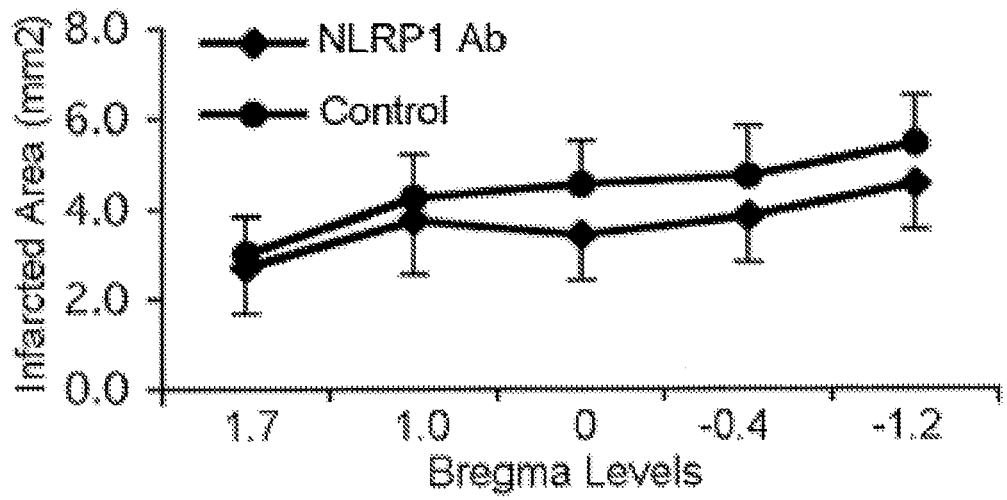
FIGS. 5A-B are graphs illustrating the effect of intraventricular injection of anti-NLRP1 antibody on infarct size.
Figure 5B:
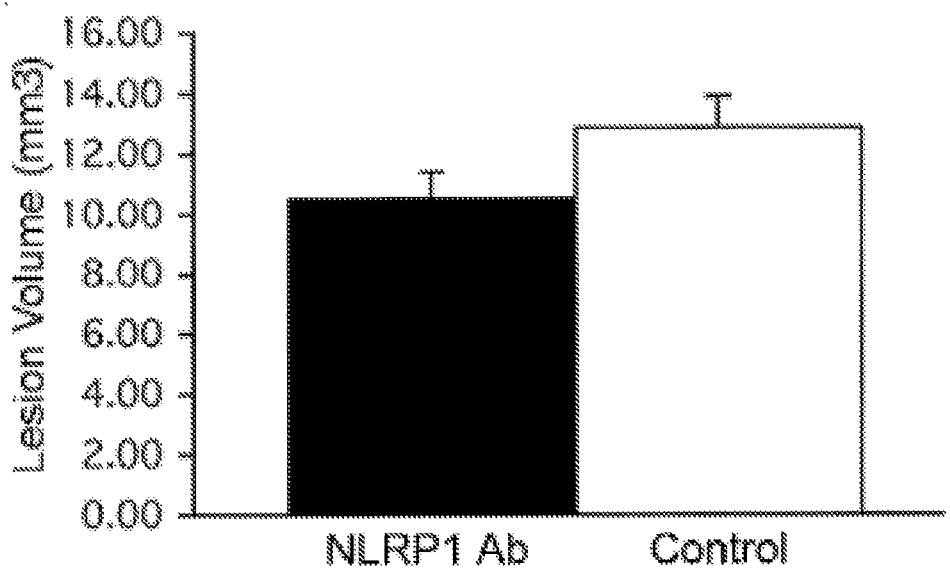

Effect of NLRP1 Neutralization on Infarct Size: Studies were conducted to determine whether this anti-NLRP1 treatment strategy would also affect infarct size. Control CCAT mice showed a pattern of well demarcated cortical infarcts within the right MCA territory as previously described (Lozano et al., J Neurosci Methods 162:244-54, 2007). Small infarcts were occasionally observed within subcortical areas, including the hippocampus, striatum and thalamus. Although all CCAT mice showed some degree of cortical infarction, infarcts were somewhat variable in size and location from mouse to mouse. This is a characteristic of the CCAT model that has previously been described in both rats and mice. In CCAT mice treated with the NLRP1 neutralizing antibody, infarct areas were considerably smaller than nontreated CCAT mice (FIG. 5). Infarct areas at 3 of the 5 analyzed bregma levels were slightly reduced by treatment, with overall infarct volume being reduced by 18% compared to nontreated mice.

Example 3

TBI Activates the NLRP1 Inflammasome in Neurons and Anti-ASC Antibody Blocks Inflammation Following TBI The results described herein and in provisional application No. 60/952,757 filed Jul. 30, 2007, which this application claims priority to are the first reports that the NLRP1 inflammasome is present in spinal cord neurons and plays an important role in the innate CNS inflammatory response after injury (Example 1). This finding indicates that microglial cells, which share properties with tissue macrophages, are not the main source of IL-1β in the brain. Indeed, IL-1β has been implicated in the pathogenesis of several neurological diseases including TBI, Alzheimer's disease, epilepsy, Parkinson's disease and stroke. Given the large number of NLR family members and their distinct but separate expression profiles in tissue, CNS cells may contain a number of yet undiscovered inflammasomes that contribute to a site-specific role in the inflammatory response. The data described herein reveals that glia express inflammasome proteins, but whether these inflammasome components form a multiprotein complex involved with inflammation is unknown. The data described herein further show that cortical neurons take up anti-ASC and neutralization of ASC after TBI results in reduced caspase-1 activation and XIAP cleavage. An improved understanding of the components of inflammasomes and the interactions that govern their function will enhance an understanding of the fundamental mechanisms of inflammatory cytokine production. The studies described herein are applicable to diverse pathologies, including CNS trauma, multiple sclerosis, Alzheimer's disease, HIV encephalitis, dementia, and ischemic injury.

Results

Traumatic injury activates caspase-1 in primary cortical neuronal cultures:

In order to determine whether stretch injury activates inflammasomes and induces inflammation in primary cultures of CNS cells, rat cortical neurons were grown on deformable SILASTIC membranes and subjected to stretch-induced injury with a pressure pulse of 50 msec. Uninjured cells in a well of the Flex Plate served as controls. Cultures were returned to the incubator, and at 1 and 2 hr after injury, cells were lysed, and caspase-1 activation was determined. Marked increases in caspase-1 processing were observed at 1 and 2 h post-injury. These studies show that mechanical injury of neurons is one signal that triggers inflammasome activation and suggest a role of inflammasome signaling in the neuronal response to brain trauma.

TBI induces processing of IL-1β in the cerebral cortex: Excessive levels of the proinflammatory cytokines IL-1β and IL-18 are associated with secondary injury following TBI. Although levels of cortical IL-1β mRNA and protein (determined by enzyme-linked immunoadsorbant assay) have been reported to rise acutely after TBI, the processing of IL-1β has not been examined by immunoblotting procedures. Therefore, in order to determine whether TBI induces the processing of IL-1β from a precursor into a mature secreted form, quantitative immunoblot analysis was performed on cortical lysates from sham-operated and traumatized animals at 15, 30 min, 1, 3, 6 and 24 hr after TBI. Within 15 min after TBI, pro-IL-1β (35 kDa) is rapidly processed to the mature form (17 kDa) in cortices of traumatized rats. These results indicate that increased levels of the mature form of IL-1β are induced rapidly within the cortex by moderate TBI and are consistent with the rapid processing and secretion observed by the vast majority of investigations studying secretion of IL-1β from primary macrophages or cell lines.

TBI induces expression of inflammasome proteins: Processing of pro-IL-1β and IL-18 involves the activation of a caspase-1-activating platform, termed the inflammasome. In order to provide direct evidence for involvement of the inflammasome in TBI-induced inflammation, traumatized cortices were analyzed for the time course of expression of key inflammatory caspases and inflammasome proteins. Antibody specificity for the reagents used was determined. TBI rapidly activated caspase-1 and upregulated caspase-11, the rodent ortholog of human caspase-5. Proteolytic processing of procaspase-1 was detected at 15 min after trauma. Accordingly, there were significant increases in the levels of the adaptor protein ASC within 1 h after TBI, whereas no significant changes in the levels of NLRP1 were observed. NLRP3 was not detected in lysates from sham and traumatized animals at any time point examined and served as a negative control. These results demonstrate that TBI rapidly stimulates expression of NLRP1 inflammasome signaling molecules.

TBI induces dramatic changes in the composition of the inflammasome:

Whether the increased expression levels of inflammasome proteins lead to formation of an inflammasome complex was next determined. The studies described above have shown that spinal cord neurons contain the NLRP1 (NALP1) inflammasome. To characterize the associations of inflammasome proteins after TBI, coimmunoprecipitations of cortical lysates from injured animals at 4 h after trauma were performed using anti-ASC antibody, anti-NLRP1 and preimmune serum as control.

In sham cortices, ASC was immunoprecipitated with anti-ASC, caspase-1, caspase-11 and pannexin-1; however very low levels of NLRP1 and XIAP were present in this signaling complex. At 4 h after TBI, the composition of the signaling complex changed. Notably, there was increased association of caspase-1, caspase-11, NLRP1, XIAP and pannexin 1 with ASC. However, the levels of full-length 53-kDa XIAP protein was cleaved to generate a 25-kDa fragment. Anti-ASC did not immunoprecipitate caspase-3, whereas preimmune serum did not immunoprecipitate the inflammasome-associated proteins, demonstrating antibody specificity, and thus serving as negative controls. In reciprocal coimmunoprecipitation experiments, anti-NLRP1 immunoprecipitated ASC, caspases-1, and -11, pannexin-1 as well as XIAP, but it did not immunoprecipitate caspase-3, thus providing additional evidence for formation of the inflammasome complex after TBI. Thus, although the levels of NLRP1 in not change at different time points after TBI, the proportion of NLRP1 recruited into the inflammasome complex increased. These findings indicate that TBI activates a molecular platform (termed the NLRP1 inflammasome) that consists of NLRP1, ASC, caspase-1, caspase-11, XIAP and pannexin-1, leading to activation of caspase-1 and cleavage of XIAP. This finding is the first report that the NLRP1 inflammasome is present in traumatized cortex and the first demonstration that pannexin-1 is part of the NLRP1 inflammasome complex.

NLRP1 Inflammasome proteins are present in cortical neurons, and TBI induces alterations in protein expression pattern: Confocal images of the cell type expression and regional distribution of NLRP1 inflammasome proteins in cortical neurons of sham animals and proteins near the injury epicenter at 4 h after injury were obtained. Sections were stained for caspase-1, caspase-11, ASC and NLRP1, and the neuronal marker MAP2. Caspase-1 immunoreactivity was seen in MAP2 positive cells, indicating that caspase-1 is expressed in neurons in the cortex of sham animals. Intense caspase-1 immunoreactivity was seen in the nucleus, and patchy staining was present in the cell cytoplasm and processes. In contrast, caspase-11 immunoreactivity demonstrated diffuse punctate staining confined to the neuronal soma and processes. Intense ASC and NLRP1 staining was detected in the soma of cortical neurons and exhibited a patchy distribution pattern, while weak NLRP1 immunoreactivity was detected in the nucleus.

Moderate TBI resulted in altered staining patterns of inflammasome proteins in cortical neurons. NLRP1 inflammasome proteins are present in cortical neurons and TBI induces alterations in protein expression patterns. Confocal images cortical neurons of sham and injured brains at 4 h posttrauma were obtained. Sections were stained for caspase-1, caspase-11, ASC and NLRP1 and the neuronal marker MAP2. In sham animals, caspase-1 immunoreactivity was seen in the nucleus. By 4 h after injury, increased caspase-1 staining was present in neuronal nuclei and patchy staining was present in the cell cytoplasm and processes near the plasma membrane. Caspase-11 immunoreactivity showed diffuse punctate staining confined to the neuronal soma and processes. Increased caspase-11 staining was present by 4 h post-trauma in the neuronal soma in a patchy distribution. Intense ASC and NLRP1 staining was detected in the soma of cortical neurons and exhibited a patchy distribution pattern in the cytoplasm. Both inflammasome proteins showed increased expression as evidenced by intense patchy staining located near or associated with the plasma membrane by 4 h post-trauma.

At 4 h after injury, increased caspase-1 immunoreactivity was present in neuronal nuclei, while intense caspase-1 staining was seen in the cell cytoplasm as large patches near the plasma membrane. Increased caspase-11 staining was present in the neuronal soma that was localized in a patchy distribution. A more striking alteration was observed in the immunostaining of ASC and NLRP1 after TBI. By 4 h after TBI, immunoreactivity of both inflammasome proteins was markedly enhanced, and intense patchy staining was seen in the neuronal soma near or associated with the plasma membrane. As shown previously, XIAP was present in the perinuclear region and cell processes of cortical neurons and TBI induced alterations in the expression pattern. The cellular distribution and location of NLRP1 inflammasome proteins near the plasma membrane of neurons after TBI is consistent with their role in the processing and secretion of IL-1 ft Anti-ASC and anti-NLRP1 antibody specificity was evaluated by preabsorption of antiserum with immunogen peptides to remove specific antibody binding (as described in Example 1). Antigen-depleted antiserum did not stain sections of sham and traumatized brains and served as a negative control (as described in Example 1). The intensity and pattern of inflammasome protein expression in neurons was altered by TBI and is consistent with the idea that neurons process and secrete IL-1β via activation of the inflammasome complex.

Inflammasome proteins are present in astrocytes and oligodendrocytes after TBI: IL-1β is synthesized by neurons and glia and is released in response to injury, insult, and stress. Beyond the function of NLRP1 in neurons (described above), no studies have heretofore identified inflammasomes in other CNS cell types or distinguished ligands and mechanisms of inflammasome activation. Confocal images of the cell type expression and regional distribution of NLRP1 inflammasome proteins in astrocytes in sham animals and astrocytes and oligodendrocytes near the injury epicenter at 6 h after TBI were obtained. Sections were stained for the astrocyte marker, glial fibrillary acid protein (GFAP) or the oligodendrocyte marker adenomatous polyposis coli (APC) clone CC1 and caspase-1 or ASC. In sham animals, ASC was not detected in astrocytes, but by 6 h after TBI; ASC was evident in some astrocytes. Caspase-1 immunoreactivity was seen in GFAP positive cells in both sham and traumatized brains at 6 h, indicating that caspase-1 is expressed in astrocytes in the cortex of sham and injured animals. ASC immunoreactivity was also seen in APC positive cells in both sham and injured cortices indicating that this inflammasome adaptor protein is expressed in oligodendrocytes. These studies provide evidence that inflammasome proteins are expressed in glia, but whether they are involved in the formation of responsive inflammasomes after TBI will be investigated in this proposal.

TBI induces caspase-1 activation in the hippocampus and thalamus: The parasagittal fluid percussion brain injury model used in these studies induces activation of apoptotic caspases not only in the cerebral cortex but also in subcortical regions including the hippocampus and thalamus (Keane et al., J Neuropathol Exp Neurol 60:422-429, 2001). In order to determine whether inflammatory caspases are induced in subcortical regions of the brain, a temporal profile was performed of the expression and activation of caspase-1 in the hippocampus and thalamus—two brain areas that show delayed neuronal damage following fluid percussion brain injury. Surprisingly, TBI rapidly activated caspase-1 and proteolytic processing of procaspase-1 was detected at 15 min after trauma in both hippocampus and thalamus and showed a similar temporal expression profile as that observed in cortex. Therefore, moderate fluid percussion brain injury activates caspase-1 in the cerebral cortex, hippocampus and thalamus.

Anti-ASC is taken up by cortical neurons: The blood-brain barrier is intact before injury and becomes disrupted by the insult. The results described above demonstrated that anti-ASC administered after SCI crossed the blood-spinal cord barrier and was taken up by spinal cord motor neurons possibly through a mechanism involving the hemichannel pannexin-1. In order to determine if cortical neurons showed a similar ability to take up anti-ASC, cortical neurons were grown in culture for 7 days. Neurons were pre-treated with cytochalasin D (endocytosis inhibitor) or carbenoxolone (nonspecific pannexin inhibitor) and then incubated with FITC-conjugated anti-ASC, FITC-conjugated actin or FITC alone. Cortical neurons incorporated FITC-conjugated anti-ASC, whereas FITC-conjugated actin and IgG was excluded from these cells. Moreover, anti-ASC uptake was abolished by pretreatment with carbenoxolone, but was not inhibited by cytochalasin D. Thus, anti-ASC is taken up by cortical neurons by a mechanism that is sensitive to carbenoxolone treatment.

Figure 6:
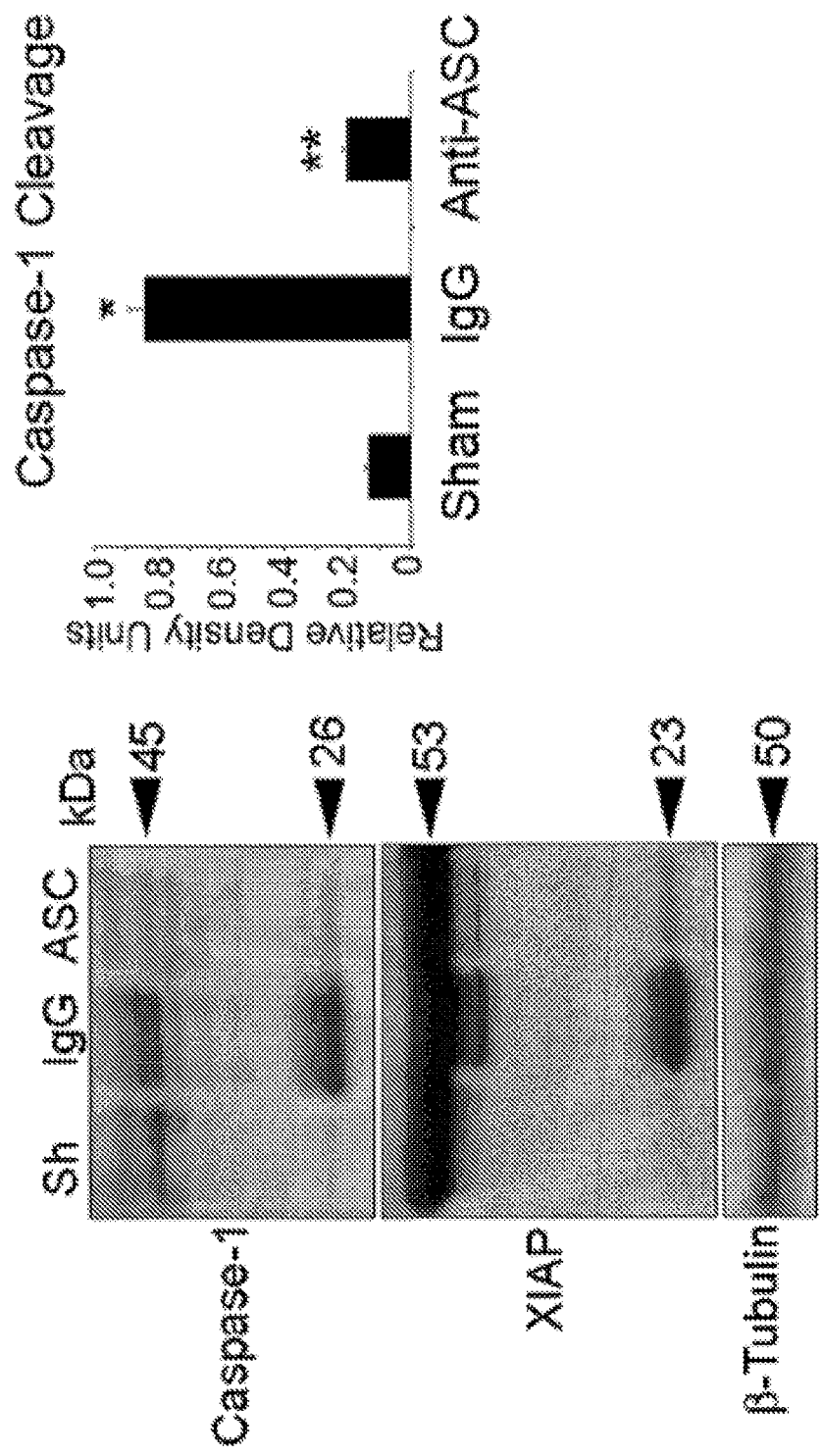
FIG. 6 is a photograph of an immunoblot and a graph illustrating that ASC neutralization decreases TBI-induced activation and processing of caspase-1 and XIAP cleavage. Representative immunoblots of injured cortices from animals subjected to TBI and treated intracerebroventricularly with antibodies to ASC (ASC), IgG controls (IgG) or left untreated (Sh) at 20 min after injury. Animals were sacrificed 24 h after treatment. Treatment resulted in inhibition of inflammasome activation as detected by a decrease in the processing of procaspase-1, and cleavage of XIAP. *p<0.05 vs sham, **p<0.05 vs IgG.

ASC neutralization reduces TBI-induced activation and processing of caspase-1 and XIAP cleavage: To dissect the contribution of the NLRP1 inflammasome to TBI-induced inflammation, the activity of the NLRP1 inflammasome was blocked with antibodies against the inflammasome adaptor protein ASC. Antibody treatment was started 20 min after trauma. One group of animals received 15 μg of anti-ASC intracerebroventricularly at 20 min after trauma (FIG. 6, ASC). Control groups received a similar treatment regimen, but using IgG of the same isotype corresponding to anti-ASC.

Cortices were removed at 24 h after treatment and lysates were prepared and immunoblotted for caspase-1 and XIAP (FIG. 6). Neutralization of ASC significantly reduced activation and processing of caspase-1, and decreased XIAP cleavage.

Other Embodiments

Any improvement may be made in part or all of the method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. For example, although the experiments described herein involved TBI, stroke and SCI, the compositions and methods described herein can find use in a number of other diseases and disorders, including autoimmune diseases and/or central nervous system diseases including ALS, Lou Gehrig's, MS, immune dysfunction muscular central nervous system breakdown, MD, AD, and PD. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method for treating inflammation associated with a central nervous system (CNS) injury or an autoimmune or neurodegenerative disease in a subject in need thereof comprising administering to the subject an antibody that specifically binds to at least one component of a mammalian inflammasome comprising Nacht Leucine-Rich-Repeat Protein 1 (NALP1), wherein the antibody specifically binds to NALP1; wherein the administering the antibody reduces levels of at least one inflammatory cytokine, thereby treating the inflammation in the patient.

2. The method of claim 1, wherein the autoimmune or neurodegenerative disease is amyotrophic lateral sclerosis, Alzheimer's disease, Parkinson's disease, muscular dystrophy, or multiple sclerosis.

3. The method of claim 1, wherein the inflammation in the CNS of the subject is reduced following administration of the antibody.

4. The method of claim 1, wherein the antibody is administered by a parenteral route of administration.

5. The method of claim 4, wherein the parenteral route of administration is intravenous, subcutaneous, intramuscular, intraperitoneal, or intrathecal.

6. The method of claim 1, wherein the antibody is administered intracerebroventricularly.

7. The method of claim 1, wherein administering the antibody results in improvement in motor skills and locomotor function or cognition in the subject.

8. The method of claim 1, wherein the antibody is a monoclonal antibody.

9. The method of claim 1, wherein the antibody is a polyclonal antibody.

10. The method of claim 1, wherein the antibody is taken up by cells in the CNS.

11. The method of claim 1, wherein administering the antibody results in inhibition of inflammasome activation in the subject.

12. The method of claim 1, wherein administering the antibody results in a reduction of caspase-1 activation and XIAP cleavage in the CNS of the subject.

13. The method of claim 1, wherein the antibody is formulated with a pharmaceutically acceptable carrier or diluent.

14. The method of claim 1, wherein the at least one component of the mammalian inflammasome is intracellular.

15. The method of claim 1, wherein the CNS injury is traumatic brain injury, stroke, or spinal cord injury.

16. The method of claim 1, wherein the at least one inflammatory cytokine is interleukin-1 β (IL-1β) or interleukin-18.

17. The method of claim 1, further comprising administering a battery of tasks to assess a functional outcome of administering the antibody.

18. The method of claim 1, wherein the antibody binds to a NALP1 amino acid sequence having at least 85% sequence identity with SEQ ID NO:3.

19. A method for treating inflammation associated with a CNS injury or an autoimmune or neurodegenerative disease in a subject in need thereof comprising administering to the subject an antibody that specifically binds to at least one component of a NALP1 mammalian inflammasome, wherein the antibody specifically binds to an amino acid sequence having at least 85% sequence identity with SEQ ID NO: 3, wherein said inflammation in said patient is treated.

* * * * *

UNITED STATES PATENT AND TRADEMARK OFFICE
CERTIFICATE OF CORRECTION

PATENT NO.         : 9,512,209 B2
APPLICATION NO.    : 14/219857
DATED              : December 6, 2016
INVENTOR(S)        : Keane et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this

Twenty-fifth Day of September, 2018

Andrei Iancu
*Director of the United States Patent and Trademark Office*

UNITED STATES PATENT AND TRADEMARK OFFICE
CERTIFICATE OF CORRECTION

PATENT NO. : 9,512,209 B2
APPLICATION NO. : 14/219857
DATED : December 6, 2016
INVENTOR(S) : Robert W. Keane et al.

Page 1 of 1

It is certified that error appears in the above-identified patent and that said Letters Patent is hereby corrected as shown below:

In the Specification

Column 1, Line 18-24:
"This invention was made with U.S. government support under grant number NS30291 awarded by the National Institutes of Health, grant number NS38865 awarded by the National Institute of Neurological Disorders and Stroke, and grant number W81XWH-05-1-6, awarded by the Department of Defense. The U.S. government has certain rights in the invention."

Should be replaced with:
--This invention was made with government support under grant number W81XWH-05-1-0001 awarded by the United States Army Medical Research Materiel Command. The government has certain rights in the invention.--

Signed and Sealed this
Ninth Day of June, 2020

Andrei Iancu
*Director of the United States Patent and Trademark Office*